United States Patent
Wu et al.

(10) Patent No.: US 11,279,678 B2
(45) Date of Patent: Mar. 22, 2022

(54) 5-FLUOROURACIL DERIVATIVES, PREPARATION METHODS AND USES THEREOF

(71) Applicant: SHANGHAI ECUST BIOMEDICINE CO., LTD., Shanghai (CN)

(72) Inventors: Fanhong Wu, Shanghai (CN); Jinwen Huang, Shanghai (CN); Jiujiu Zhou, Shanghai (CN); Wan Pang, Shanghai (CN); Lei Zhao, Shanghai (CN); Zhonglin Ma, Shanghai (CN); Zhikai Zhang, Shanghai (CN); Xiaodong Yu, Shanghai (CN); Jianyue Wu, Shanghai (CN)

(*) Notice: Subject to any disclaimer, the term of this patent is extended or adjusted under 35 U.S.C. 154(b) by 77 days.

(21) Appl. No.: 16/762,238

(22) PCT Filed: Nov. 9, 2017

(86) PCT No.: PCT/CN2017/110104
§ 371 (c)(1),
(2) Date: May 7, 2020

(87) PCT Pub. No.: WO2019/090558
PCT Pub. Date: May 16, 2019

(65) Prior Publication Data
US 2021/0230122 A1   Jul. 29, 2021

(51) Int. Cl.
*C07D 239/30* (2006.01)
*C07D 239/553* (2006.01)
*A61K 31/505* (2006.01)
*A61P 35/00* (2006.01)

(52) U.S. Cl.
CPC .......... *C07D 239/553* (2013.01); *A61P 35/00* (2018.01)

(58) Field of Classification Search
CPC .................. C07D 239/30; C07D 239/553; A61K 31/505; A61P 35/00
See application file for complete search history.

(56) References Cited

FOREIGN PATENT DOCUMENTS

CN   101723813 A   6/2010
CN   107311846 A   11/2017

OTHER PUBLICATIONS

New Drugs. Dec. 31, 2011 (Dec. 31, 2011), 20(17), ISSN: 1003-3734, p. 1711, paragraph 1 to p. 1712, paragraph 1, and p. 1712, figure 1. (WU, Min et al. Synthesis and Anti tumor Effect of (5-Fluorouracil-1Acetic Acid)-4'-Curcuminate.).

*Primary Examiner* — Bruck Kifle
(74) *Attorney, Agent, or Firm* — OPES IP Consulting Co. Ltd.

(57) ABSTRACT

Disclosed is a 5-fluorouracil derivative having the molecular structure shown in general formula VI, in which Ra and Rb groups are an alkoxy group or a fluorine-substituted alkoxy group having 1, 2, 3, or 4 carbon atoms, and are mono-, bis-, tri-, tetra- or penta-substituted on a phenyl group; a linking group L1 is an alkyl or alkenyl group having 1, 2, 3, or 4 carbon atoms, a linking group L2 is oxygen, or an alkyl or alkoxy group having 1, 2, 3, or 4 carbon atoms, or an amino acid, or an alkyl group having 1, 2, 3, or 4 carbon atoms containing an amino moiety, or a furyl group, and an X group is O or —NH—. Further disclosed is a method for preparing such a derivative and a use of the same in the treatment of cancer, tumor diseases, and diseases caused by abnormal neovascularization in a human or non-human mammal, and a medicament or a composition containing the 5-fluorouracil derivative.

7 Claims, No Drawings

5-FLUOROURACIL DERIVATIVES, PREPARATION METHODS AND USES THEREOF

FIELD

This invention belongs to the field of pharmaceutical chemistry, in particular to anti-tumor compounds, preparation methods of the compounds and pharmaceutical uses thereof.

BACKGROUND

Folkman first put forward the theory of angiogenesis in 1971. He believed that tumor vascular system plays an important role in the process of tumor growth, development and metastasis. It can inhibit tumor angiogenesis and lead to partial death of tumor cells due to ischemia and hypoxia, thus delaying tumor growth and inhibiting tumor metastasis (Folkman J. er al., J. Med 1971, 285, 1182-1186). Pharmacological studies confirm that tumor growth must depend on angiogenesis, which provides a new target for tumor therapy. The research and development of tumor vascular targeting drugs has become a research hotspot of anti-tumor drugs. In the 1980s, American scientists reported that a series of stilbene compounds with antitumor activity were isolated from the trunk of a South African plant (Combretum cafprum)(Srivastava v. et al., bioorg. Med. Chem. 2005, 135892-5908). The results showed that these compounds could not only block tumor angiogenesis but also inhibit the aggregation of tubulin The action of tubulin is similar to colchicine, among which combretastatin A-4 (Abbreviation: CA4) has the best activity. Because of its strong liposolubility and poor water solubility, CA4 can be directly used as a drug for development and research. Oxigene, a pharmaceutical company, has developed CA4 as a precursor of water-soluble sodium phosphate (Combretastatin A-4 phosphate, CA4P). At present, the compound has entered phase III clinical research.

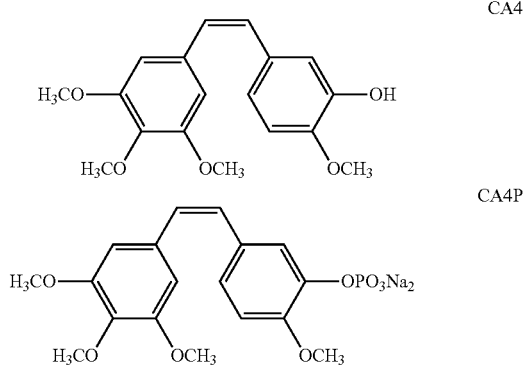

In recent years, the study of structural modification based on the chemical structure and anti-tumor mechanism of CA4 has become a hot topic in the research of anti-tumor drugs. CA4 compounds have the same structural characteristics as other tubulin inhibitors, i.e. diaryl bridges. Among them, the rind which has three methoxy ring is A-ring and the other is B-ring (Medarde M. et al., Bioorg. Med. Chem. Lett., 1999, 9, 2303-2308). One of the research focuses of structural modification is the modification or replacement of the connecting segments between two rings. The results show that the activity of cis double bond stilbene is significantly higher than that of trans double bond compounds (Cushman M. et al., J. Med. Chem. 1991, 34, 2579-2588; Nam N. H., et al. Bioorg. Med. Lett., 2002, 12, 1955-1958). There are many reports about the introduction of substituents on double bonds, but the activity of the synthesized derivatives is not high (Hadfield J. A., et al., Eur. J. Med. Chem., 2005, 40, 529-541; Pinney K. G. et al., Bioorg. Med. Chem., 2000, 8, 2417-2425). The alkene bond was replaced by saturated carbon chain. The results of activity experiments showed that the activity of the two carbon number compounds was retained or increased, while the basic activity of other compounds was lost (Getahum Z. et al., J. Med. Chem. 1992, 35, 1058-1067).

Currently, only the stilbene compound CA4 has entered the clinical research. The invention patent application "THE PREPARATION AND THE USE OF ETHOXY COMBRETASTATINS AND THEIR PRODRUGS" (International Publication No. WO2008/031333A1) has disclosed that the 4'-alkoxy group in B ring of CA4 is an active action site, and the original 4'-methyloxy group in B ring of stilbene is transformed into ethyloxy group. This ethyloxy group with 3-hydroxyl group and amino group can form active target, which can improve its targeting activity towards tumor blood vessel.

We found that the 4'-alkoxy group and 3'-hydroxy group of the diphenylethane derivatives formed by hydrogenation of the double bonds of the stilbene compounds 3, 4, 5-trimethoxy-3'-hydroxy-4'-alkoxy diphenyl ethane have the same synergistic effect, and the antitumor effect is significantly improved compared with CA4 (Fanhong W U etc. Ethoxy Diphenyl Ethane Derivatives, Preparation Processes and Uses Thereof, Publication No. US2012/0046492A1; A preparation method of 3, 4, 5-trimethoxy-3'-hydroxy-4'-alkoxy diphenyl ethane, Publication No. CN103539642)

After the double bond was transformed into saturated bond, the related physicochemical properties were more stable than CA4 due to the absence of cis-trans isomer changes, the preparation process of the compound was simpler, the synthesis yield was significantly increased, and the raw material loss and unit synthesis cost were greatly reduced.

5-fluorouracil (5-FU) is a traditional anti-tumor drug commonly used in clinic. As an important water-soluble anti metabolism drug, because of the stable C—F bond structure and the enhancement of acid, it can be more firmly combined with enzyme, can replace the important precursor of tumor nucleic acid, and can also block the methylation of 5-uracil and inhibit the synthesis of DNA, so as to play an anti-tumor role. It is widely used in breast cancer, colorectal cancer and gastric cancer. However, due to its significant first pass metabolism and low lipophilicity, its oral absorption is incomplete, rectal administration absorption is worse, bioavailability is low, which affects the anti-tumor effect, and its treatment dose is close to the toxic dose. In order to overcome the above shortcomings, as well as the side effects of vomiting, diarrhea, hair loss, leukocyte and platelet decline, central neurotoxicity and so on in clinical application, a lot of researches have been carried out on it, and some derivatives with better efficacy and less side effects have been developed, mainly improving the biological activity, selectivity, liposolubility, absorption performance and low toxicity of 5-fluorouracil. Among them, there are two typical 5-fluorouracil derivatives, Floxuridine and Tegafur, which are widely used in clinic.

In the development of new drugs, the principle of combination is one of the most common and important methods.

The application of the splicing method is mainly to develop drugs with double effects, including the effect with different receptors, the effect with two different binding sites of one receptor, the effect with two different enzymes or the effect with one receptor of one enzyme. It is possible to obtain new antitumor drugs with higher activity, lower side effects and better drug resistance. Splicing 5-FU with other antitumor drugs has been a hot topic in the field of drug research. Menger spliced 5-FU and cytarabine to obtain a new 5-FU derivative, which is still stable at high pH value Menger, F. M.; Rourk, M. J. Synthesis and Reactivity of 5-Fluorouracil/Cytarabine Mutual Prodrugs. J. Org. Chem., 1997, 62, 9083.) Podophyllotoxin has anti-virus and anti-tumor activities. It is used to treat many kinds of tumors, but its clinical application is limited because of its typical side effects. Chen prepared a series of spliced products of podophyllotoxin and 5-FU. SAR study shows that the use of different amino acids has a great impact on the activity. The hydroxyl of amino acid branch chain will significantly reduce the activity, while there is no significant effect on activity with growth of alkyl linkers (Chen, S. W.; Xiang, R.; Liu, J.; Tian, X. Synthesis and biological evaluation of novel conjugates of podophyllotoxin and 5-FU as antineoplastic agents. W. Bioorg. Med. Chem., 2009, 17, 3111.) Camptothecin is a cytotoxin alkaloid with high antitumor activity targeting at topoisomerase I. However, due to its extremely low water solubility and unstable lactone structure, its clinical application is limited. Zhou et al. Prepared the splicing products of camptothecin and 5-FU with dipeptide as the linker, which improves tumor selectivity and safety (Zhou, W. M.; He, R. R.; Ye, J. T.; Zhang, N.; Liu, D. Y. Synthesis and Biological Evaluation of New 5-Fluorouracil-Substituted Ampelopsin Derivatives [J]. Molecules., 2010, 15, 2114).

SUMMARY

In the field of research and development of anticancer and antitumor drugs, researchers have realized that stilbene derivatives, diphenylethane derivatives and 5-fluorouracil have good therapeutic effects on tumors, but their respective defects also exist objectively.

By comparing the advantages and disadvantages of their antitumor effects, we found that they have complementary possibilities. Stilbene derivatives/diphenylethane derivatives have different antitumor mechanisms from 5-FU, but both of them have good antitumor activity in vitro, good complementarity in the mode of action, and better efficacy in combination. We creatively combined stilbene derivatives/diphenylethane derivatives with 5-fluorouracil through amide bond to form a novel antitumor drug molecule. At the same time, through the subsequent biological activity test, we found that the new compound has the advantages of two kinds of antitumor drugs, achieves the purpose of synergistic effect, and has a good prospect of application and development.

In the invention, we provide the following 7 technical solutions:

Technical Solution I

The invention provides a 5-fluorouracil derivatives, the molecular structure of which is shown in the general formula VI:

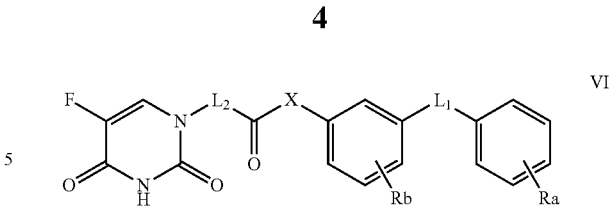

wherein:
1) Ra is a mono-substituted, di-substituted, tri-substituted, tetra-substituted or penta-substituted group, in which the substituent group is independently (C1-C4) alkoxy, or fluorine-substituted (C1-C4) alkoxy;
2) Rb is mono-substituted, di-substituted, tri-substituted, tetra-substituted or penta-substituted group, in which the substituent group is independently (C1-C4) alkoxy, or fluorine-substituted (C1-C4) alkoxy;
3) the linking group L1 is independently —$C_nH_{2n}$— (n=1, 2, 3, 4), or —CH=CH$C_nH_{2n}$— (n=0, 1, 2);
4) the linking group L2 is independently selected from the group of a bond, —O—, —$C_nH_{2n}$— (n=1, 2, 3, 4), —O$C_nH_{2n}$— (n=1, 2, 3, 4), amino acid, (C1-C4) alkyl with amino, or furanyl;
5) the group X is independently selected from the group of a bond, O, —NH—.

The 5-fluorouracil derivatives provided by the invention could further has characteristic as follows:
wherein:
1) Ra is a tri-substituted group, in which the substituent group are —OMe, —OCF$_3$, —OCF$_2$H or —OCFH$_2$,
2) Rb is a mono-substituted phenyl, in which the substituent group is —OMe, or —OEt,
3) the linking group L1 is independently —CH$_2$CH$_2$—, —CH=CH,
4) the linking group L2 is the group of a bond, —R(C1-C4)-.

The 5-fluorouracil derivatives provided by the invention could further has characteristic as follows:
its structure characteristic is shown as formula I:

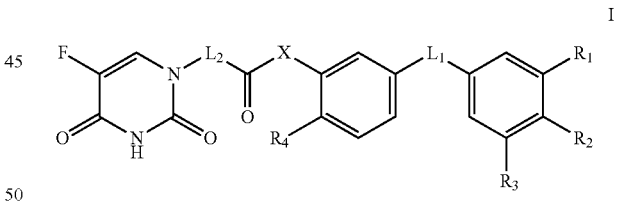

wherein:
1) each R1, R2 or R3 is independently (C1-C4) alkoxy, or fluorine-substituted (C1-C4) alkoxy;
2) R4 is independently (C1-C4) alkoxy, or fluorine-substituted (C1-C4) alkoxy;
3) the linking group L1 is independently —$C_nH_{2n}$— (n=1, 2, 3, 4), —CH=CH$C_nH_{2n}$— (n=0, 1, 2);
4) the linking group L2 is the group of a bond, —O—, —$C_nH_{2n}$— (n=1, 2, 3, 4), —O$C_nH_{2n}$— (n=1, 2, 3, 4), amino acid, (C1-C4) alkyl with amino, or furanyl; 5) each X is independently selected from the group of a bond, —O—, —NH—.

The 5-fluorouracil derivatives provided by the invention could further has characteristic as follows:
wherein: each R1, R2, R3 or R4 is independently —OCH$_3$, —OC$_2$H$_5$, —OCF$_3$, —OCF$_2$H or —OCFH$_2$;

the linking group L1 is independently —CH$_2$CH$_2$— or —CH═CH—;

the L2 is the group of a bond, —C$_n$H$_{2n}$— (n=1, 2, 3), cyclopropyl.

The 5-fluorouracil derivatives provided by the invention could further has characteristic as follows:

Compound Ia: (Z)-3-(5-fluoro-2,4-dioxo-3,4-dihydropyrimidin-1(2H)-yl)-N-(2-methoxy-5-(3,4,5-trimethoxystyryl (phenyl) acetamide;
Compound Ib: 3-(5-fluoro-2,4-dioxo-3,4-dihydropyrimidin-1(2H)-yl)-N-(2-methoxy-5-(3,4,5-trimethoxyphenethyl (phenyl) acetamide;
Compound Ic: (Z)-4-(5-fluoro-2,4-dioxo-3,4-dihydropyrimidin-1(2H)-yl)-N-(2-methoxy-5-(3,4,5-trimethoxystyryl(phenyl) propanamide;
Compound Id: 3-(5-fluoro-2,4-dioxo-3,4-dihydropyrimidin-1(2H)-yl)-N-(2-methoxy-5-(3,4,5-trimethoxyphenethyl (phenyl) propanamide;
Compound Ie: (Z)-4-(5-fluoro-2,4-dioxo-3,4-dihydropyrimidin-1(2H)-yl)-N-(2-methoxy-5-(3,4,5-trimethoxystyryl(phenyl)butyrylamide;
Compound If: 4-(5-fluoro-2,4-dioxo-3,4-dihydropyrimidin-1(2H)-yl)-N-(2-methoxy-5-(3,4,5-trimethoxyphenethyl (phenyl)butyrylamide;
Compound Ig: N-(2-ethoxy-5-(3,4,5-trimethoxyphenethyl (phenyl)-2-(5-fluoro-2,4-dioxo-3,4-dihydropyrimidin-1 (2H)-yl) acetamide;
Compound Ih: N-(2-ethoxy-5-(3,4,5-trimethoxyphenethyl (phenyl)-3-(5-fluoro-2,4-dioxo-3,4-dihydropyrimidin-1 (2H)-yl) propanamide;
Compound Ii: (Z)-2-methoxy-5-(3,4,5-trimethoxystyryl)-phenyl-2-(5-fluoro-2,4-dioxo-3,4-dihydropyrimidin-1 (2H)-yl)acetate;
Compound Ij: 2-methoxy-5-(3,4,5-trimethoxyphenethyl)-phenyl-2-(5-fluoro-2,4-dioxo-3,4-dihydropyrimidin-1 (2H)-yl)acetate;
Compound Ik: (Z)-2-methoxy-5-(3,4,5-trimethoxystyryl)-phenyl-3-(5-fluoro-2,4-dioxo-3,4-dihydropyrimidin-1 (2H)-yl)propanoate;
Compound Il: 2-methoxy-5-(3,4,5-trimethoxyphenethyl)-phenyl-3-(5-fluoro-2,4-dioxo-3,4-dihydropyrimidin-1 (2H)-yl)propanoate;
Compound Im: (Z)-2-methoxy-5-(3,4,5-trimethoxystyryl)-phenyl-4-(5-fluoro-2,4-dioxo-3,4-dihydropyrimidin-1 (2H)-yl)butyrate;
Compound In: 2-ethoxy-5-(3,4,5-trimethoxyphenethyl)-phenyl-2-(5-fluoro-2,4-dioxo-3,4-dihydropyrimidin-1 (2H)-yl)acetate;
Compound Io: 2-ethoxy-5-(3,4,5-trimethoxyphenethyl)-phenyl-2-(5-fluoro-2,4-dioxo-3,4-dihydropyrimidin-1 (2H)-yl)propanoate.

Technical Solution II

The invention provides the preparation method of compounds with formula (I), its characteristic is that compounds are obtained by carboxyl condensation of raw materials II and intermediates III under the action of condensation reagents:

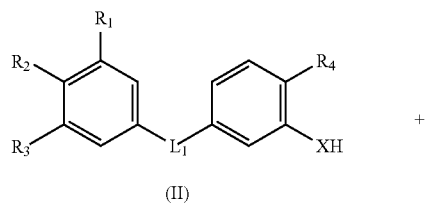

(II)

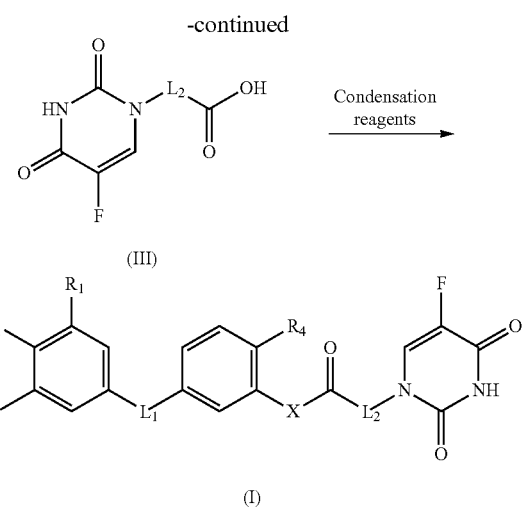

wherein:
1) each R1, R2 or R3 is independently (C1-C4) alkoxy, or fluorine-substituted (C1-C4) alkoxy;
2) R4 is independently (C1-C4) alkoxy, or fluorine-substituted (C1-C4) alkoxy;
3) the linking group L1 is independently —C$_n$H$_{2n}$— (n=1, 2, 3, 4), —CH═CHC$_n$H$_{2n}$— (n=0, 1, 2);
4) the linking group L2 is the group of a bond, —O—, —C$_n$H$_{2n}$— (n=1, 2, 3, 4), —OC$_n$H$_{2n}$— (n=1, 2, 3, 4), amino acid, (C1-C4) alkyl with amino, or furanyl;
5) each X is independently selected from the group of a bond, —O—, —NH—.

The preparation method provided by the invention could further has characteristic as follows, wherein the specific steps are as follows:

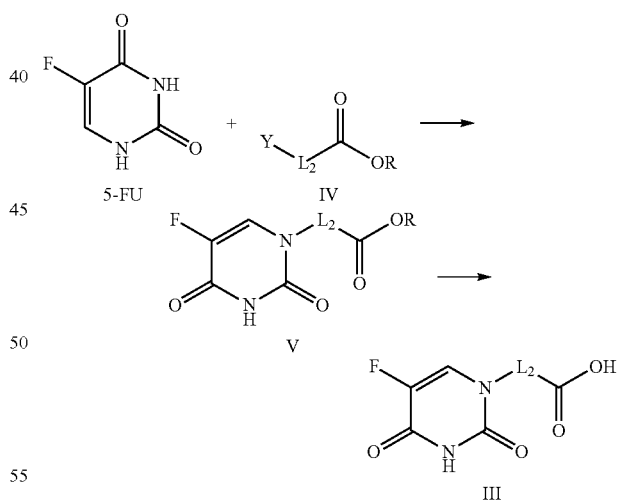

1) the intermediates V is prepared from the alkylation reaction of 5-fluorouracil (5-FU) with raw material IV;
2) the intermediates III is obtained from the hydrolysis reaction of the intermediates V.

Wherein: Each Y in raw material IV is independently Cl, Br or I.

Each R in raw material IV is independently CH$_3$, CH$_2$CH$_3$, CH$_2$CH$_2$CH$_3$ or CH(CH$_3$)$_2$.

Wherein: above condensation reagent is DCC, EDCI, BOP, PyBOP, HBTU or HATU.

DCC, Dicyclohexylcarbodiimide.

EDCI, 1-(3-DiMethylaMinopropyl)-3-ethylcarbodiiMide.

BOP, Benzotriazollyloxy)tris(dimethylamino)phosphonium hexafluophosphate.

PyBOP, Benzotriazol-1-yl-oxytripyrrolidinophosphonium hexafluorophosphate.

HBTU, O-Benzotriazole-N,N,N',N'-tetramethyl-uronium-Hexafluorophosphate.

HATU, 1-[Bis(dimethylamino)methylene]-1H-1,2,3-triazolo [4,5-b]pyridinium 3-oxid hexafluorophosphate.

Technical Solution III

The invention also provides the application of 5-fluorouracil derivatives in the treatment of cancer and tumor diseases of human or non-human mammals, including lung cancer, non-small cell lung cancer, liver cancer, pancreatic cancer, gastric cancer, bone cancer, esophageal cancer, breast cancer, prostate cancer, testicular cancer, colon cancer, ovarian cancer, bladder cancer, cervical cancer, black Melanoma, squamous cell carcinoma, basal cell carcinoma, adenocarcinoma, sweat adenocarcinoma, sebaceous adenocarcinoma, papillary carcinoma, papillary adenocarcinoma, cystic adenocarcinoma, cystic carcinoma, medullary carcinoma, bronchial carcinoma, bone cell carcinoma, epithelial carcinoma, cholangiocarcinoma, choriocarcinoma, embryo carcinoma, seminoma, verms carcinoma, gliocarcinoma, astrocytoma, neuroblastoma, craniopharyngioma, ventricular Angioma, pineal tumor, hematoblastoma, vocal cord neuroma, meningioma, neuroblastoma, optic neurocytoma, retinoblastoma, neurofibroma, fibrosarcoma, fibrocytoma, fibroadenoma, fibrochondroma, fibrocystic tumor, fibromyxoma, fibroosteoma, fibromyxosarcoma, fibropapilloma, mucosarcoma Mucinous cystoma, mucinous chondroma, mucinous chondrosarcoma, mucinous chondrofibrosarcoma, mucinous adenoma, mucoblastoma, liposarcoma, lipoma, fatty adenoma, lipochondroma, fatty chondroma, fatty fibroma, fatty hemangioma, mucinous lipoma, chondrosarcoma, chondroma, chondromyoma, chordoma, chorioadenoma, Chorioepithelioma, Chorioepithelioma Cytoma, osteosarcoma, osteoblastoma, osteochondrofibroma, osteochondrosarcoma, osteochondroma, osteocystis, osteoodontoma, osteofibroma, osteofibrosarcoma, angiosarcoma, hemangioma, angiolipoma, angiochondroma, hemangioblastoma, hemangioblastoma, angiokeratoma, angioneurogliomas, hemangioendothelioma, angiofibroma, angiolipoma Angiolymphangioma, angiolipoleiomyoma, angiomyolipoma, angioneuroma, angiomyxoma, angioreticuloendothelioma, lymphangiosarcoma, lymphogranuloma, lymphangioma, lymphoma, lymphangiomyxoma, lymosarcoma, lymphangiofibroma, lymphangiocytoma, lymphoepithelioma, lymphoblastoma, endothelial tumor, endothelial cell tumor, synovial tumor Synovial sarcoma, mesothelioma, connective tissue tumor, Ewing tumor, leiomyoma, leiomyosarcoma, adult leiomyoma, smooth muscle fibroma, rhabdomyoma, rhabdomyosarcoma, rhabdomyomyxoma, acute lymphoblastic leukemia, acute myeloid leukemia, chronic disease cell/erythrocytosis, lymphoma or multiple myeloma.

Technical Solution IV

The invention also provides the use of 5-fluorouracil derivative in the technical solution I, which includes:

as the use of tubulin aggregation inhibitors or the preparation of tubulin aggregation inhibitors;

it can be used as an anti-tumor vascular destroyer or as an anti-tumor vascular destroyer in the preparation of drugs with vascular targeting effect on various tumors;

use for the treatment of diseases caused by abnormal neovascularization or the preparation of drugs for the treatment of diseases caused by abnormal neovascularization, among them, the diseases caused by abnormal neovascularization include rheumatoid arthritis, diabetic retinopathy, prematurity retinopathy, retinal vein occlusion, psoriasis, rosacea, Kaposi's sarcoma, specific reactive keratitis, epidemic keratoconjunctivitis, neovascularized glaucoma, bacterial ulcer, fungal ulcer, simple scar rash infection, band scar rash Infection, protozoa infection, Mycobacterium infection, polyarteritis, sarcoid tumor, scleritis, crimson, dry mouth and dry eye arthritis syndrome, systemic lupus erythematosus, AIDS syndrome, syphilis.

Technical Solution V

The invention also provides a treatment method for diseases, that is, the 5-fluorouracil derivative in the first technical solution alone or various cancers and tumor diseases combined with other anti-cancer drugs and anti-tumor drugs for treating human or non-human mammals.

Among them, various tumors and cancers include lung cancer, non-small cell lung cancer, liver cancer, pancreatic cancer, gastric cancer, bone cancer, esophageal cancer, breast cancer, prostate cancer, testicular cancer, colon cancer, ovarian cancer, bladder cancer, cervical cancer, melanoma, squamous cell cancer, basal cell cancer, adenocarcinoma, sweat adenocarcinoma, sebaceous adenocarcinoma, papillary cancer, papillary adenocarcinoma, cystic adenocarcinoma, cystic carcinoma Cancer, medullary cancer, bronchial cancer, bone cell cancer, epithelial cancer, cholangiocarcinoma, choriocarcinoma, embryo cancer, spermatogonial cancer, Wilms cancer, glioblastoma, astrocytoma, neuroblastoma, craniopharyngioma, ependymoma, pineal tumor, hematoblastoma, vocal cord neuroma, meningioma, neuroblastoma, optic neurocytoma, retinal cell Tumor, neurofibroma, fibrosarcoma, fibroblastoma, fibroma, fibroadenoma, fibrochondroma, fibrocystic tumor, fibromyxoma, fibroosteoma, fibromyxosarcoma, fibropapilloma, mucosarcoma, mucosarcoma, mucosarcoma, mucosarchondrosis sarcoma, mucosarchondrosis fibrosarcoma, mucosarcoma, mucosarcoma, liposarcoma, lipoma Fatty adenoma, lipoblastoma, lipochondroma, lipofibroma, lipoangioma, myxolipoma, chondrosarcoma, chondromyoma, chordoma, chorioadenoma, Chorioepithelioma, choriocytoma, osteosarcoma, osteosarcoma, osteosarcoma, osteochondroma, osteosarcoma, osteofibroma, osteofibroma Fibrosarcoma, angiosarcoma, hemangioma, angiolipoma, angiochondroma, hemangioblastoma, angiokeratoma, angioglioma, hemangioendothelioma, angiofibroma, angiomyoma, angiolipoma, angiolymphangioma, angiolipoleiomyoma, angiomyolipoma, angiomyoneuroma, angiomyxoma, angioreticuloendothelioma, lymphangioma Sarcoma, lymphogranuloma, lymphangioma, lymphoma, lymphomyxoma, lymphosarcoma, lymphangiofibroma, lymphoma, lymphoepithelioma, lymphoblastoma, endothelioma, endothelioma, synovial tumor, synovial sarcoma, mesothelioma, connective tissue tumor, Ewing tumor, leiomyoma, leiomyosarcoma, smooth muscle fibroma, rhabdomyoma Tumor, rhabdomyosarcoma, rhabdomyomyxoma, acute lymphoblastic leukemia, acute myeloid leukemia, chronic cell/erythrocytosis, lymphoma or multiple myeloma.

Technical Solution VI

The invention also provides a medicine or a pharmaceutical composition, which comprises a 5-fluorouracil derivative in technical solution I.

The dosage form of the medicine or pharmaceutical composition of the invention is selected from the following dosage forms: lyophilized powder, powder, injection, liposome, emulsion, microcapsule, suspension or solution for intravenous administration; granule, tablet, capsule or syrup for oral administration; or suppository.

Technical Solution VII

The invention also provides a treatment method for cancer and tumor diseases of human or non-human mammals, which is characterized in that the drug is administered once every 48 hours, seven times in 12 consecutive days.

The drug in the administration is the drug or pharmaceutical composition in the technical solution VI, and the 5-fluorouracil derivatives in the technical solution I is 25-50 mg/kg in weight per administration.

Among them, cancer and tumor include lung cancer, non-small cell lung cancer, liver cancer, pancreatic cancer, gastric cancer, bone cancer, esophageal cancer, breast cancer, prostate cancer, testicular cancer, colon cancer, ovarian cancer, bladder cancer, neck cancer, melanoma, squamous cell cancer, basal cell cancer, adenocarcinoma, sweat adenocarcinoma, sebaceous adenocarcinoma, papillary carcinoma, papillary adenocarcinoma, cystic adenocarcinoma, cystic carcinoma Myeloid carcinoma, bronchial carcinoma, bone cell carcinoma, epithelial carcinoma, cholangiocarcinoma, choriocarcinoma, embryo carcinoma, spermatogonial carcinoma, Wilms carcinoma, glioblastoma, astrocytoma, neuroblastoma, craniopharyngioma, ependymoma, pineal tumor, hematoblastoma, vocal cord neuroma, meningioma, neuroblastoma, optic neurocytoma, retinoblastoma Neurofibroma, fibrosarcoma, fibroblastoma, fibroma, fibroadenoma, fibrochondroma, fibrocystic tumor, fibromyxoma, fibroosteoma, fibromyxosarcoma, fibropapilloma, mucosarcoma, mucosarcoma, mucosarchondroma, mucosarcoma, mucosarchondrosis fibrosarcoma, mucosarcoma, mucosarcoma, liposarcoma, lipoma Fatty adenoma, lipoblastoma, lipochondroma, lipofibroma, fatty hemangioma, myxolipoma, chondrosarcoma, chondromyoma, chordoma, chorioadenoma, Chorioepithelioma, choriocytoma, osteosarcoma, osteosarcoma, osteosarcoma, osteochondrofibroma, osteochondrosarcoma, osteochondroma, osteoodontoma, osteofibroma, osteofibroma Sarcoma, angiosarcoma, hemangioma, angiolipoma, angiochondroma, hemangioblastoma, angiokeratoma, angioglioma, hemangioendothelioma, angiofibroma, angiomyoma, angiolipoma, angiolymphangioma, angiolipoleiomyoma, angiomyolipoma, angiomyoneuroma, angiomyxoma, angioreticuloendothelioma, lymphangiosarcoma Lymphogranuloma, lymphangioma, lymphoma, lymphangiomyxoma, lymphosarcoma, lymphangiofibroma, lymphoma, lymphoepithelioma, lymphoblastoma, endothelial tumor, endothelial cell tumor, synovial tumor, synovial sarcoma, mesothelioma, connective tissue tumor, Ewing tumor, leiomyoma, leiomyosarcoma, smooth muscle fibroma, rhabdomyoma Rhabdomyosarcoma, rhabdomyomyxoma, acute lymphoblastic leukemia, acute myeloid leukemia, chronic cell/erythrocytosis, lymphoma or multiple myeloma.

Function and Effect of Invention

In the biological activity test experiment, CA4 and 5-fluorouracil as positive control drug are used together with the splices of the two types of antitumor drug as general formula I of the present invention to evaluate the proliferation inhibition activity of HeLa cervical cancer cell line in vitro (MTT method). Under the same experimental conditions, the IC50 values of 5-fluorouracil and CA4 were 113.24 and 400 nM, respectively, while the IC50 values of all splices were below 70 nM. Among them, proliferation inhibitory activity in vitro on HeLa cervical cancer cell line of the most active compounds is 4 times as much as that of 5-fluorouracil and 14 times as much as that of CA4.

Two splices were selected to further investigate the antitumor activities of four other tumor cell lines (MCG-803, HepG2, A549, MDA-MA-231). Compared with the positive drugs CA4 and 5-fluorouracil, the activity of the spliced product was significantly improved, which indicated that the spliced product had synergistic effect in vivo.

Furthermore, it was found that the number of alkyl carbons (n=1, 2, 3, 4) on the linker L2 had a certain effect on the activity of the product. Generally speaking, the activity was better when n=2.

Two compounds with strong activity in vitro were selected to study tumor inhibitory effect of MGC-803 on transplanted tumor in mice. The tumor inhibition rate was more than 80% at the oral administration of 50 mg/kg, and the effective oral dose was about one tenth of the LD50 value of 5-fluorouracil (230 mg/kg), which had good safety.

5-fluorouracil is an anti metabolic anti-tumor drug, which has a wide anti-tumor spectrum, while bone marrow suppression and severe gastrointestinal reactions and other side effects/adverse reactions reduce the patient's tolerance to treatment. The water-solubility of this kind of compounds is high and the liposoluble is poor. As a kind of tubulin inhibitor, stilbene/Diphenylethanes compounds have tumor blood vessel targeting, high liposolubility and poor water solubility. The invention splices two anti-tumor drugs with different mechanism of action in the form of chemical bond, which can improve their respective pharmaceutical properties, improve the anti-tumor activity and oral bioavailability of stilbenes/Diphenylethanes compounds. In addition, through the vascular targeting effect of stilbenes/Diphenylethanes 5-fluorouracil can be directed to tumor cells, thus reducing the side effects of 5-fluorouracil.

Therefore, the new structural compounds I obtained by splicing two kinds of anti-tumor drugs have the anti-tumor effects of two kinds of anti-tumor drugs, and the side effect is smaller than that of 5-fluorouracil.

DETAILED DESCRIPTION

This invention provides preparation methods of compounds with formula I, which are obtained by carboxyl condensation of raw materials II and intermediates III under the action of condensation reagent, as follows:

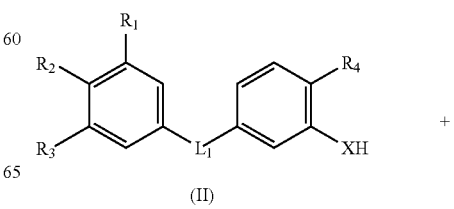

(II)

-continued

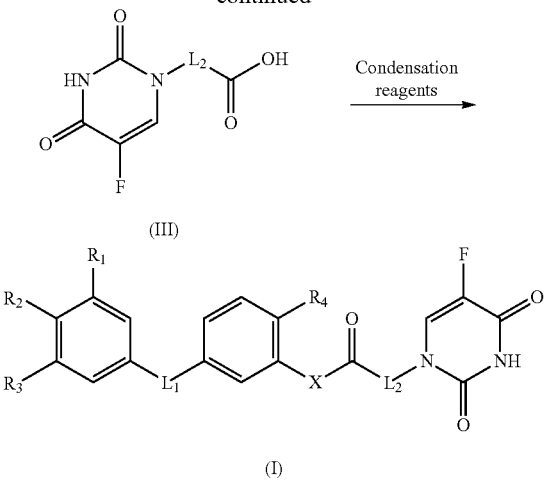

Wherein:

1) Each R1, R2 or R3 is independently (C1-C4) alkoxy, or fluorine-substituted (C1-C4) alkoxy.

2) Each R4 is independently selected from (C1-C4) alkoxy, or fluorine-substituted (C1-C4) alkoxy.

3) The linking group L1 is independently (C1-C4) alkyl or (C1-C4) alkenyl.

4) Each L2 is independently selected from the group of a bond, O, (C1-C4) alkyl, (C1-C4) alkoxy, amino acid, (C1-C4) alkyl with amino, or furanyl.

5) Each X is independently selected from the group of a bond, O, NH.

6) The condensation reagent is independently DCC, EDCI, BOP, PyBOP, HBTU or HATU, preferably DCC.

In this embodiment, the synthesis route of raw material II of stilbenes and diphenylethanes is as follows:

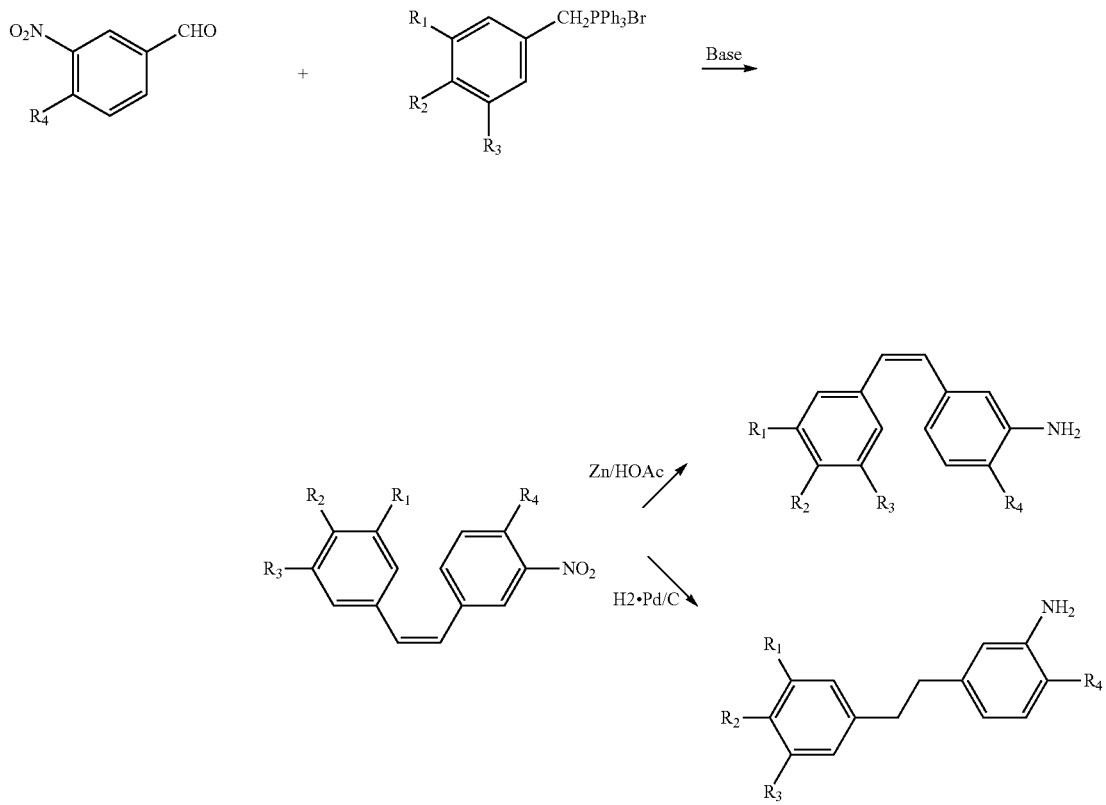

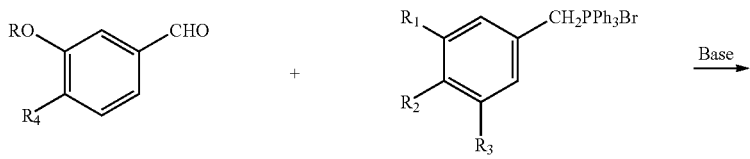

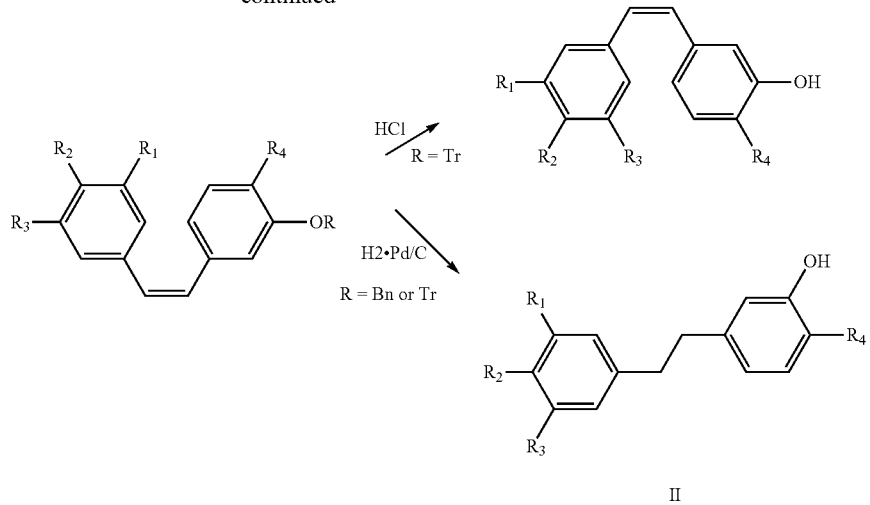

1) Each R1, R2 or R3 is independently (C1-C4) alkoxy, or fluorine-substituted (C1-C4) alkoxy.

2) Each R4 is independently selected from (C1-C4) alkoxy, or fluorine-substituted (C1-C4) alkoxy.

The detailed synthesis method about raw material II of stilbenes and diphenylethanes used in the invention has been described in patents US2012/0046492A1 and CN103539642 by the inventor.

The intermediate III of 5-fluorouracil involved in this embodiment is a known compound, which is prepared by the following steps slightly improved according to literature:

1) 5-fluorouracil (5-FU) reacts with raw material IV to afford intermediate V.

2) Intermediate V is hydrolyzed to afford intermediate III.

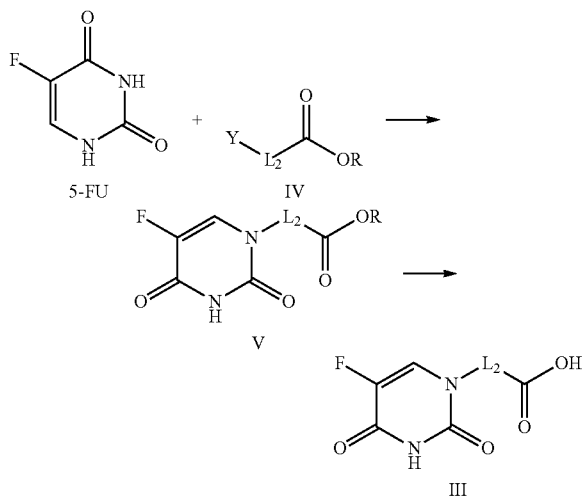

Wherein, Y in raw material IV is selected from chlorine, bromine or iodine, preferably chlorine and bromine. The linking group L2 is the group of a bond, —O—, —$C_nH_{2n}$— (n=1, 2, 3, 4), —$OC_nH_{2n}$— (n=1, 2, 3, 4), amino acid, (C1-C4) alkyl with amino, or furanyl.

Each R is hydrogen, methyl, ethyl, propyl or isopropyl, preferably hydrogen, methyl and ethyl.

In order to further understanding of the technical content of the invention, the synthesis methods of raw material II of stilbenes or diphenylethanes and 5-fluorouracil intermediate III used in the invention are illustrated with examples as follows:

Preparation of Raw Material II of Stilbenes or Diphenylethanes

Example 1: Preparation of 3'-amino-3,4,4',5-tetramethoxystilbene (IIa)

Step 1: Synthesis of 3'-nitro-3,4,4',5-tetramethoxystilbene

Under nitrogen, 3,4,5-trimethoxybenzylbromotriphenylphosphonate (4.42 g, 8.5 mmol) was suspended in anhydrous tetrahydrofuran (50 ml). the mixture was cooled to −20° C., and n-butyl lithium solution (8 ml, 2.5 m) was added dropwise slowly. After adding, the reactant was keep stirring for 3 h. A tetrahydrofuran (10 mL) solution of 3-nitro-4-methoxy benzaldehyde (1.5 g, 8.3 mmol) was added to the reaction solution through a drop funnel. After adding, the reaction was keep for 5 h, the reactant was raised to room temperature and reacted overnight. While TLC test showed that the reaction was complete, water (50 ml) was added to quench reaction and the organic solution was separated. The water layer was exacted by ethyl acetate (50 ml). The organic phase was combined and washed with water for 2 or 3 time, and was dried with anhydrous sodium sulfate. The oil was obtained by rotary evaporation. The residue was crystallized with anhydrous ethanol to obtain a solid of 3'-nitro-3,4,4', 5-tetramethoxystilbene (1.6 g, 46%). 1H-NMR (500 MHz, CDCl3) δ8.03 (s, 1H), 7.68 (d, J=5 Hz, 1H), 7.11 (d, J=10 Hz, 1H), 7.00 (m, 2H), 6.75 (s, 2H), 4.01 (s, 3H), 3.94 (s, 6H), 3.90 (s, 3H).

Step 2: Preparation of 3'-amino-3,4,4', 5-tetramethoxystilbene

3'-nitro-3,4,4',5-tetramethoxystilbene (1.4 g, 4.0 mmol) obtained in step 1 was dissolved in acetic acid (10 ml). Zinc powder (6.5 g) was added the solution, and the reactant was stirred and reacted at room temperature for 2 h. While TLC test showed that the reaction was complete, the mixture was filtrated. The filtration was pour to water (50 ml). The water layer extracted with dichloromethane (3*50 mL). The combined organic phase was washed with saturated sodium bicarbonate solution, saturated brine and water once respectively, dried with anhydrous sodium sulfate, filtered and concentrated under vacuum to afford the product IIa (0.9 g, 70.2%). 1H-NMR (500 MHz, CDCl3) δ6.95 (s, 1H), 6.91 (m, 3H), 6.89 (d, J=5 Hz, 1H), 6.80 (d, J=5 Hz, 1H), 6.73 (s, 2H), 3.93 (s, 3H), 3.90 (s, 6H), 3.88 (s, 3H).

Example 2: Preparation of 3'-amino-3,4,4',5-tetramethoxy diphenylethane (IIb)

3'-nitro-3,4,4',5-tetramethylstilbene (1.4 g, 4.0 mmol) prepared in step 1 of example 1 was dissolved with ethyl acetate (30 mL), and 10% Pd—C catalyst (200 mg) was added. The reaction system was replaced with hydrogen three times. The hydrogenate reaction was maintained at room temperature for 4 h. While the reaction detected by TLC was complete the reactant was filtered. The filtrate was concentrated under vacuum. The crude residue was subjected to column chromatography to afford the product IIb (1 g, 78.0%). 1H-NMR (500 MHz, CDCl3) δ6.95 (s, 1H), 6.91 (m, 3H), 6.89 (d, J=5 Hz, 1H), 6.80 (d, J=5 Hz, 1H), 6.73 (s, 2H), 3.93 (s, 3H), 3.90 (s, 6H), 3.88 (s, 3H).

Example 3: Preparation of 3'-amino-4'-ethoxy-3,4,5-trimethoxy stilbene (IIc)

Step 1: Preparation of 3'-nitro-4'-ethoxy-3,4,5-trimethoxystilbene (3,4,5-trimethoxybenzyl)triphenylphosphonium bromide (15 g, 28.7 mmol) was suspended in anhydrous tetrahydrofuran (300 mL) under argon. The mixture was cooled to −15° C., and n-butyllithium cyclohexane solution (1.6 mol/L, 22 mL) was added dropwise. After the reactant was stirred for 1 hour, tetrahydrofuran (24 mL) solution of 4-ethoxy-3-nitrobenzaldehyde (5.7 g, 29 mmol) was slowly dropped into the reaction solution. The reactant was stirred for 1 hour and then stirred overnight at room temperature. While TLC test showed that the reaction was complete, water was added to quench reaction and the organic solution was separated. Three fours of the solvent was removed by concentration. The remaining mother liquor was crystallized using 4 times anhydrous ethanol in ice bath and then filtered to afford light yellow solid of the product (6.8 g, 65%).

Step 2: Synthesis of 3'-amino-4'-ethoxy-3,4,5-trimethoxystilbene

3'-nitro-4'-ethoxy-3,4,5-trimethoxystilbene (1.4 g, 4.0 mmol) obtained in step 1 was dissolved in acetic acid (10 ml). Zinc powder (6.5 g) was added into the solution, and the reactant was stirred at room temperature for 2 h. While TLC test showed that the reaction was complete, the mixture was filtrated. The filtration was pour to water (50 ml) and neutralized with sodium hydroxide until pH=9. The organic layer extracted with dichloromethane was washed with saturated brine dried with anhydrous sodium sulfate, filtered and concentrated under vacuum to afford the product IIc (1.1 g).

Example 4: Preparation of 3'-amino-4'-ethoxy-3,4,5-trimethoxy diphenylethane (IId)

3'-amino-4'-ethoxy-3,4,5-trimethoxystilbene (2 g) prepared in step 2 of example 3 was dissolved with ethyl acetate (50 mL), and 10% Pd—C catalyst (500 mg) was added. The reaction system was replaced with hydrogen three times. The hydrogenate reaction was maintained at room temperature for 4 h. While the reaction detected by TLC was complete the reactant was filtered. The filtrate was concentrated under vacuum to afford the product II d.

1H-NMR (500 MHz, CDCl3) δ7.14 (d, 1H, 2'-H), 6.88 (d, 1H, 6'-H), 6.68 (d, 1H, 5'-H), 6.60 (s, 2H, 2, 6-H); 4.48 (brs, 2H, NH2); 4.08 (q, 2H, —CH2), 3.77 (s, 3H, 4-OCH3), 3.75 (s, 6H, 3, 5-OCH3), 2.85 (d, 1H, J=12.5 Hz, 1a-H); 2.78 (d, 1H, J=12.5 Hz, 1a'-H), 1.56 (3H, t; CH3); MS (m/Z): 331 (M+); HRMS, Calcd: 331.1784, found: 331.1753.

Example 5: Preparation of 3'-hydroxyl-3,4,4',5-tetramethoxy diphenylethane (IIe)

Step 1: Synthesis of 3'-benzyloxy-3,4,4',5-tetramethoxystilbene

Dried THF (50 mL) and (3,4,5-trimethoxybenzyl)triphenyl phosphonium bromide (4.42 g, 8.5 mmol) were added to a three-necked flask filled by nitrogen and cooled to −20° C. After the mixture was stirred for 1 h, 2.5M n-butyllithium (8 mL) was added slowly and the reactant continued stirring for 3 h. A THF (10 mL) solution of 3-benzyloxy-4-methoxybenzaldehyde (1.21 g, 5 mmol) was dropped and the resulting reaction mixture was stirred for 5 h. The mixture was warmed to room temperature and stirred overnight. After reaction detected by TLC was complete, water (100 mL) was added to stop the reaction and the organic liquid was separated. The water layer was extracted with EA (50 mL). The combined organic phases was washed with water for 2-3 times, dried with anhydrous sodium sulfate, and concentrated under vacuum. The residue was disposed with anhydrous ethanol (15 mL) to afford the product (1.2 g, 59%). 1H-NMR (500 MHz, CDCl3) δ3.91 (s, 9H); 5.20 (s, 2H); 6.70 (s, 2H); 6.83 (d, J=16.5 Hz, 1H); 6.90 (m, 2H); 7.08 (t, J=8.5 Hz, 2H); 7.32 (t, J=7.5 Hz, 1H); 7.39 (t, J=7.5 Hz, 2H); 7.48 (d, J=7.5 Hz, 2H).

Step 2: Preparation of 3'-hydroxyl-3,4,4'5-tetramethoxy diphenylethane (IIe)

Anhydrous ethanol (60 mL) and 3'-benzyloxy-3,4,4',5-tetramethoxystilbene (2.03 g, 5 mmol) were added to a three-necked flask filled with hydrogen at room temperature. 10% Pd—C (0.5 g) was added and acetic acid (1 mL) was added dropwise. After the reactant reacted for 4 hours, TLC detection showed that the reaction was complete. Pd—C was removed by filtration and the filtrate was concentrated to remove most of the solvent. The residue was leave overnight in refrigerator. A lot of crystals precipitated was filtered to afford the product Ie (1.4 g, 88%). 1H-NMR (500 MHz, CDCl3), δ2.82 (s, 4H); 3.85 (d, J=10 Hz, 12H); 5.61 (s, 1H); 6.38 (s, 2H); 6.65 (dd, J=2.0 Hz, J=8.0 Hz, 1H); 6.77 (d, J=8.0 Hz, 1H); 6.81 (d, J=2.0 Hz, 1H).

Example 6: Preparation of 3'-hydroxyl-4'-ethoxy-3,4,5-trimethoxy diphenylethane (IIf)

Step 1: Preparation of 3'-benzyloxy-4'-ethoxy-3,4,5-trimethoxystilbene 3,4,5-trimethoxybenzyl triphenylphosphonium bromide (20 g, 38.2 mmol) was suspended in anhydrous tetrahydrofuran (150 mL). Solid potassium tert-butoxide (7.5 g, 66.5 mmol) was added to the reaction solution in batches with stirring. The raw materials were gradually dissolved after stirring at room temperature for 30 min, and the reaction system turned to blood red. Tetrahydrofuran (70 mL) solution dissolved 4-ethoxy-3-benzyloxybenzaldehyde (10.5 g, 41.0 mmol) was added through dropping funnel. The mixture was stirred at room temperature for another 1 h after dropping. After reaction detected by TLC was complete, deionized water (140 mL) was added and the organic liquid was separated. The water layer was extracted with diethyl ether (2*300 mL). The combined organic phases was dried with anhydrous magnesium sulfate and filter cake was washed diethyl ether (50 mL). The filtrate was concentrated to afford oily matter (25 g). The oily matter was disposed with anhydrous ethanol (20 mL) to afford a pale yellow solid (14.1 g). The solid was recrystallized by anhydrous ethanol (25 mL) and then washed with anhydrous ether (10 mL), dried to afford a pale yellow powder of pure 3'-benzyloxy-4'-ethoxy-3,4,5-trimethoxy stilbene (10.6 g, 61.6%).

Step 2: Preparation of 3'-hydroxyl-4'-ethoxy-3,4,5-trimethoxy diphenylethane (IIf)

Ethyl acetate (200 mL) and 3'-benzyloxy-4'-ethoxy-3,4,5-trimethoxy stilbene (10.6 g, 25.8 mmol) prepared in step 1 were added to a flask filled with hydrogen. 10% Pd—C (1 g) was added. The reaction system was replace with hydrogen three times, then the reactant reacted for 1 hours at room temperature. The mixture was filtered and the filtrate was concentrated. The residue was recrystallized with 40 mL ethanol and washed with ethanol to afford the product IIf of white crystal (6.7 g, 83%)

Preparation of Intermediates III 5-Fluorouracil

Example 1: Preparation of 2-(5-fluorouracil) acetic acid (IIIa)

Potassium hydroxide (19.2 g, 0.34 mol), water (80 mL) and 5-fluorouracil (13.0 g, 0.1 mol) were added to a flask. The reactant was stirred to dissolve and was warmed to 80° C. Bromide acetic acid (18.1 g, 0.13 mol) was slowly added dropwise and then reactant was stirred for 4 hours. While the reaction detected by TLC was complete, the reactant was cooled to room temperature and the pH of the mixture was adjusted to 2 with concentrated hydrochloric acid. Solid precipitated with ice bath cooling was filtrated and recrystallized using hot water to afford product IIIa (12.1 g, 64.4%). 1H-NMR (500 MHz, D2O) δ7.72 (d, J=5 Hz, 1H), 4.43 (s, 2H).

Example 2: Preparation of 3-(5-fluorouracil) Propionic acid (IIIb)

Step 1: Preparation of 3-(5-fluorouracil) ethyl propionate 5-fluorouracil (13.0 g, 0.1 mol), DMF (300 mL), ethyl 3-bromopropanoate (21.5, 0.12 mol) and potassium carbonate (13.8 g, 0.1 mol) were added to a flask. The mixture was stirred for 18 hours at room temperature. While the reaction detected by TLC was complete, the reactant was poured to water. The water layer was extracted with ethyl acetate. The organic phase was washed by saturation brine 2 or 3 times, dried by sodium sulfate and concentrated at vacuum. The yellow oil was subjected to column chromatography to afford a colorless crystal of 3-(5-fluorouracil) ethyl propionate (12.5 g, 54.3%). 1H-NMR (500 MHz, CDCl3) δ9.94 (s, 1H), 7.58 (d, J=5 Hz, 1H), 4.18 (q, J=5 Hz, 2H), 3.98 (t, J=5 Hz, 2H), 2.80 (t, J=5 Hz, 2H), 1.28 (t, J=5 Hz, 3H).

Step 2: Preparation of 3-(5-fluorouracil) Propionic acid (IIIb)

Distilled water (40 mL), 3-(5-fluorouracil) ethyl propionate (4.6 g, 20 mmol) and 2M sodium hydroxide (20 mL) were added to flask and stirred. The reactant was heated to reflux for 2 h. While the reaction detected by TLC was complete, the mixture was adjusted with concentrated hydrochloric acid to pH=1. Solid obtained by concentrated was recrystallized with water to afford white solid of IIIb (2.6 g, 64.4%). 1H-NMR (500 MHz, D2O) δ7.82 (d, J=5 Hz, 1H), 3.92 (t, J=5 Hz, 2H), 2.73 (t, J=5 Hz, 2H).

Example 3: Preparation of 4-(5-fluorouracil) butyric acid (IIIc)

Step 1: Preparation of 4-(5-fluorouracil) ethyl butyrate

According to step 1 in Example 2 of Preparation of intermediates III, ethyl 4-bromobutanoate was reacted with 5-fluorouracil to afford 4-(5-fluorouracil) ethyl butyrate. 1H-NMR (500 MHz, CDCl3) δ9.08 (s, 1H), 7.34 (d, J=5 Hz, 1H), 4.17 (q, J=5 Hz, 2H), 3.81 (t, J=5 Hz, 2H), 2.41 (t, J=5 Hz, 2H), 2.04 (m, 2H), 1.29 (t, J=5 Hz, 3H).

Step 2: Preparation of 4-(5-fluorouracil) butyric acid (IIIc)

According to step 2 in Example 2 of Preparation of intermediates III, 4-(5-fluorouracil) ethyl butyrate was hydrolysised with 1M Sodium hydroxide solution to afford 4-(5-fluorouracil) butyric acid (IIIc). 1H-NMR (500 MHz, CDCl3) δ7.78 (d, J=5 Hz, 1H), 3.73 (t, J=5 Hz, 2H), 2.37 (t, J=5 Hz, 2H), 1.91 (m, 1H).

Preparation Embodiment for 5-Fluorouracil Derivative in Technical Solution 1

Embodiment 1: Preparation of (Z)-2-(5-fluoro-2,4-dioxo-3,4-dihydropyrimidin-1(2H)-yl)-N-(2-methoxy-5-(3,4,5-trimethoxystyryl)-phenyl)acetamide (Ia)

3,4,4',5-tetramethoxy-3'-aminostilbene (IIa, 0.5 g, 1.57 mmol), 2-(5-fluorouracil) acetic acid (IIIa, 1.0 g, 5.31 mmol) and 30 mL anhydrous methylene chloride were added into a flask filled with nitrogen. The mixture was stirred to dissolve, DCC (0.8 g) was added and was stirred at room temperature for 24 hours. While the reaction detected by TLC was complete, the mixture was filtered and filtrate was concentrated. The residue was subjected to column chromatography to afford product Ia (0.26 g). 1H-NMR (500 MHz, CDCl3) δ 8.30 (s, 1H), 8.23 (s, 1H), 8.13 (s, 1H), 7.44 (d, J=5 Hz, 1H), 6.91 (d, J=5 Hz, 1H), 6.83 (d, J=5 Hz, 1H), 6.40 (s, 2H), 4.54 (s, 2H), 3.91 (s, 3H), 3.84 (s, 9H), 2.84 (s, 4H). 13C-NMR (100 MHz, DMSO-d6) δ166.23, 158.10, 157.84, 153.46, 150.25, 149.41, 140.78, 138.51, 137.40, 133.36, 131.83, 131.50, 129.96, 128.01, 127.48, 126.89, 123.61, 119.35, 111.85, 104.02, 60.49, 56.30, 50.77; HRMS-ESI (m/z): [M+H]+ (Calcd for C24H25N3O8F) 486.1677;

Found 486.1667. [M+Na]+ (Calcd for C24H24N3O8FNa) 508.1496; Found 508.1494. FTIR (KBr, cm-1) 1126.43, 1217.08, 1251.80, 1267.23, 1352.10, 1419.61, 1444.68, 1463.97, 1492.90, 1506.41, 1543.05, 1589.34, 1660.71, 1699.29, 1712.79, 2985.81, 3026.31, 3061.03.

Embodiment 2: Preparation of 2-(5-fluoro-2,4-di-oxo-3,4-dihydropyrimidin-1(2H)-yl)-N-(5-(3,4,5-trimethoxyphenethyl)-2-methoxyphenyl)-acetamide (Ib)

According to Embodiment 1, 3,4,4',5-tetramethoxy-3'-amino diphenylethane (IIb, 0.5 g, 1.57 mmol) was reacted with 2-(5-fluorouracil) acetic acid (IIIa, 1.0 g, 5.31 mmol). The crude was subjected to column chromatography to afford product Ib (0.35 g). 1H-NMR (500 MHz, CDCl3) δ8.76 (s, 1H), 8.57 (s, 1H), 8.19 (s, 1H), 7.44 (d, J=5 Hz, 1H), 7.23 (d, J=5 Hz, 1H), 6.96 (s, 2H), 6.91 (d, J=5 Hz, 1H), 6.73 (s, 2H), 4.56 (s, 2H), 3.95 (s, 3H), 3.93 (s, 6H), 3.88 (s, 3H). 13C-NMR (100 MHz, DMSO-d6) δ166.00, 158.10, 157.84, 153.07, 150.23, 148.03, 140.76, 138.50, 137.64, 136.00, 133.88, 131.83, 131.50, 126.96, 124.75, 122.10, 111.47, 106.03, 60.36, 56.17, 50.73, 38.27, 37.11. HRMS-ESI (m/z): [M+H]+ (Calcd for C24H27N3O8F) 488.1833; Found 488.1845. [M+Na]+ (Calcd for C24H26N3O8FNa) 510.1652; Found 510.1646; FTIR (KBr, cm-1) 1002.98, 1024.20, 1126.43, 1217.08, 1251.80, 1267.23, 1352.10, 1382.96, 1419.61, 1444.68, 1463.97, 1492.90, 1506.41, 1543.05, 1589.34, 1660.71, 1699.29, 1712.79, 3026.31.

Embodiment 3: Preparation of 3-(5-fluoro-2,4-di-oxo-3,4-dihydropyrimidin-1(2H)-yl)-N-(5-(3,4,5-trimethoxystyryl)-2-methoxyphenyl)-propanamide (Ic)

According to Embodiment 1, 3,4,4',5-tetramethoxy-3'-aminophenylethane (IIa, 0.5 g, 1.57 mmol) was reacted with 3-(5-fluorouracil) Propionic acid (IIIb, 1.0 g, 5.31 mmol). The crude was subjected to column chromatography to afford product Ic (0.29 g). 1H-NMR (300 MHz, DMSO-d6) δ11.77 (s, 1H), 9.31 (s, 1H), 8.07 (s, 1H), 8.00 (d, J=3 Hz, 1H), 7.27 (d, J=3 Hz, 1H), 7.13 (d, J=15 Hz, 1H), 7.01 (d, J=6 Hz, 1H), 6.93 (s, 1H), 6.87 (s, 2H), 3.89 (t, J=6 Hz, 2H), 3.79 (s, 9H), 3.63 (s, 3H), 2.78 (t, J=6 Hz, 2H). 13C-NMR (100 MHz, DMSO-d6) δ169.36, 158.04, 157.79, 153.47, 150.07, 149.89, 140.78, 138.51, 137.43, 133.39, 131.29, 130.96, 129.87, 127.99, 127.53, 126.98, 123.50, 120.75, 111.83, 104.05, 60.49, 56.29, 56.20, 45.25, 35.28. HRMS-ESI (m/z): [M+H]+ (Calcd for C24H26N2O8F) 500.1883; Found 500.1905. [M+Na]+ (Calcd for C24H25N2O8FNa) 522.1652; Found 522.1655; FTIR (KBr, cm-1) 834.52, 1012.73, 1028.85, 1117.61, 1159.22, 1176.58, 1198.32, 1248.56, 1325.34, 1353.69, 1424.23, 1465.11, 1471.69, 1534.29, 1586.20, 1662.64, 1685.79, 1714.83, 2913.27, 3023.45.

Embodiment 4: Preparation of 3-(5-fluoro-2,4-di-oxo-3,4-dihydropyrimidin-1(2H)-yl) N-(5-(3,4,5-trimethoxyphenethyl)-2-methoxyphenyl)-propana-mide (Id)

According to Embodiment 1, 3,4,4',5-tetramethoxy-3'-amino diphenylethane (IIb, 0.5 g, 1.57 mmol) was reacted with 3-(5-fluorouracil) Propionic acid (IIIb, 1.0 g, 5.31 mmol). The crude was subjected to column chromatography to afford product Id (0.32 g). 1H-NMR (500 MHz, CDCl3) δ8.34 (s, 1H), 8.21 (s, 1H), 7.79 (s, 1H), 7.69 (d, J=5 Hz, 1H), 6.90 (d, J=5 Hz, 1H), 6.82 (d, J=5 Hz, 1H), 6.44 (s, 2H), 4.11 (t, J=5 Hz, 2H), 3.88 (s, 3H), 3.87 (s, 6H), 3.85 (s, 3H), 2.92 (t, J=5 Hz, 2H), 2.88 (d, J=5 Hz, 4H). 13C-NMR (100 MHz, DMSO-d6) δ169.36, 167.88, 158.11, 157.86, 153.46, 153.38, 149.91, 140.69, 138.53, 137.42, 133.38, 131.22, 129.87, 127.98, 127.53, 126.96, 123.49, 120.75, 111.82, 104.04, 60.48, 56.29, 56.20, 49.99, 32.05, 30.72, 25.81. HRMS-ESI (m/z): [M+H]+ (Calcd for C24H26N2O8F) 502.1990; Found 502.2035. [M+Na]+ (Calcd for C24H25N2O8FNa) 524.1809; Found 524.1810; FTIR (KBr, cm-1) 804.32, 1010.70, 1028.06, 1118.71, 1159.22, 1176.58, 1192.01, 1242.16, 1323.17, 1357.89, 1427.32, 1460.11, 1471.69, 1485.19, 1512.19, 1539.20, 1593.20, 1662.64, 1685.79, 1708.93, 2843.07, 3003.17.

Embodiment 5: Preparation of 4-(5-fluoro-2,4-di-oxo-3,4-dihydropyrimidin-1(2H)-yl)-N-(5-(3,4,5-trimethoxystyryl)-2-methoxyphenyl)-butanamide (Ie)

According to Embodiment 1, 3,4,4',5-tetramethoxy-3'-aminophenylethane (IIa, 0.5 g, 1.57 mmol) was reacted with 4-(5-fluorouracil) butyric acid (III c, 1.0 g, 5.31 mmol). The crude was subjected to column chromatography to afford product Ie (0.29 g). 1H-NMR (500 MHz, CDCl3) δ 8.30 (s, 1H), 8.23 (s, 1H), 8.13 (s, 1H), 7.44 (d, J=5 Hz, 1H), 6.91 (d, J=5 Hz, 1H), 6.83 (d, J=5 Hz, 1H), 6.40 (s, 2H), 4.54 (s, 2H), 3.91 (s, 3H), 3.84 (s, 9H), 2.84 (s, 4H). 13C-NMR (100 MHz, DMSO-d6) δ171.03, 158.05, 157.80, 153.46, 150.07, 141.14, 138.87, 137.39, 133.42, 130.78, 130.45, 129.83, 128.10, 127.85, 126.86, 123.17, 120.35, 111.70, 106.43, 104.03, 60.49, 56.30, 56.22, 55.98, 47.88, 33.26, 24.57. HRMS-ESI (m/z): [M+H]+ (Calcd for C26H29N2O8F) 514.1990; Found 514.1971. [M+Na]+ (Calcd for C26H28N2O8FNa) 536.1809; Found 536.1810. FTIR (KBr, cm-1) 866.04, 891.11, 968.27, 1016.49, 1029.99, 1116.78, 1159.22, 1184.29, 1201.65, 1215.15, 1236.37, 1253.73, 1284.59, 1328.95, 1350.17, 1363.67, 1421.54, 1429.25, 1471.69, 1506.41, 1529.55, 1581.63, 1668.43, 1685.79, 1718.58, 2943.37, 3047.53.

Embodiment 6: Preparation of 4-(5-fluoro-2,4-di-oxo-3,4-dihydropyrimidin-1(2H)-yl)-N-(5-(3,4,5-trimethoxyphenethyl)-2-methoxyphenyl)-butana-mide (If)

According to Embodiment 1, 3,4,4',5-tetramethoxy-3'-aminodiphenylethane (IIb, 0.5 g, 1.57 mmol) was reacted with 4-(5-fluorouracil) butyric acid (IIIc, 1.0 g, 5.31 mmol). The crude was subjected to column chromatography to afford product If (0.37 g). 1H-NMR (500 MHz, CDCl3) δ8.61 (s, 1H), 8.44 (s, 1H), 7.86 (d, J=5 Hz, 1H), 7.22 (d, J=5 Hz, 1H), 6.99 (2H, s), 6.90 (d, J=10 Hz, 1H), 6.76 (s, 2H), 3.90 (s, 3H), 3.86 (s, 6H), 3.85 (s, 3H), 2.55 (t, J=5 Hz, 2H), 2.17 (t, J=5 Hz, 2H), 1.27 (m, 2H). 13C-NMR (100 MHz, DMSO-d6) δ170.90, 158.02, 157.77, 153.04, 150.43, 150.09, 141.25, 139.34, 137.18, 132.38, 129.95, 129.87, 128.68, 127.79, 123.15, 113.09, 106.32, 60.47, 56.30, 55.98, 47.39, 33.79, 32.11, 30.54, 24.06. HRMS-ESI (m/z): [M+H]+ (Calcd for C26H31N2O8F) 516.2146; Found 516.2138. [M+Na]+ (Calcd for C26H30N2O8FNa) 538.1965; Found 538.1968. FTIR (KBr, cm-1) 891.11, 968.27, 1016.49, 1029.99, 1116.78, 1159.22, 1184.29, 1201.65, 1215.15, 1236.37, 1253.73, 1284.59, 1328.95, 1350.17, 1363.67, 1421.54, 1429.25, 1471.69, 1506.41, 1529.55, 1581.63, 1668.43, 1685.79, 1718.58, 2943.37, 3047.53.

Embodiment 7: Preparation of N-(5-(3,4,5-trimethoxyphenethyl)-2-ethoxyphenyl)-2-(5-fluoro-2,4-dioxo-3,4-dihydropyrimidin-1(2H)-yl)acetamide (Ig)

According to Embodiment 1, 3,4,5-trimethoxy-3'-amino-4'-ethoxy diphenylethane (IIc, 0.5 g, 1.57 mmol) was reacted with 2-(5-fluorouracil) acetic acid (IIIc, 1.0 g, 5.31 mmol). The crude was subjected to column chromatography to afford product Ig (0.36 g). 1H-NMR (300 MHz, DMSO-d6) δ11.86 (s, 1H), 9.37 (s, 1H), 8.06 (d, J=6 Hz, 1H), 7.86 (s, 1H), 6.91 (m, 2H), 6.49 (s, 2H), 4.56 (s, 2H), 4.05 (q, J=6 Hz, 2H), 3.69 (s, 6H), 3.56 (s, 3H), 2.72 (s, 4H), 1.24 (t, J=6 Hz, 3H). 13C-NMR (100 MHz, DMSO-d6) δ165.93, 158.08, 157.83, 153.06, 150.23, 147.20, 140.78, 138.51, 137.65, 135.99, 133.84, 131.81, 131.47, 127.71, 127.19, 124.84, 122.21, 119.58, 112.66, 110.05, 106.04, 64.48, 60.37, 56.18, 50.80, 38.25, 37.13, 15.04. HRMS-ESI (m/z): [M+H]+ (Calcd for C26H31N2O8F) 502.1990; Found 502.1956. [M+Na]+ (Calcd for C26H30N2O8FNa) 524.1809; Found 524.1812. FTIR (KBr, cm-1) 1010.70, 1045.42, 1093.64, 1145.72, 1161.15, 1172.72, 1234.44, 1251.80, 1269.16, 1311.59, 1328.95, 1363.67, 1396.46, 1427.32, 1452.40, 1465.90, 1514.12, 1593.20, 1683.86, 1720.50, 1743.65, 2929.87, 2943.37, 2964.59, 3003.17, 3064.89.

Embodiment 8: Preparation of N-(5-(3,4,5-trimethoxyphenethyl)-2-ethoxyphenyl)-3-(5-fluoro-2,4-dioxo-3,4-dihydropyrimidin-1(2H)-yl)propanamide (Ih)

According to Embodiment 1, 3,4,5-trimethoxy-3'-amino-4'-ethoxy diphenylethane (IIc, 0.5 g, 1.57 mmol) was reacted with 3-(5-fluorouracil) propanoic acid (IIIc, 1.0 g, 5.31 mmol). The crude was subjected to column chromatography to afford product Ig (0.41 g). 1H-NMR (300 MHz, DMSO-d6) δ11.77 (s, 1H), 9.05 (s, 1H), 7.98 (d, J=6 Hz, 2H), 7.74 (s, 1H), 6.88 (s, 2H), 6.49 (s, 2H), 3.99 (q, J=6 Hz, 2H), 3.88 (t, J=3 Hz, 2H), 3.70 (s, 6H), 3.58 (s, 3H), 2.77 (t, J=6 Hz, 2H), 2.73 (s, 4H), 1.28 (t, J=6 Hz, 3H). 13C-NMR (100 MHz, DMSO-d6) δ172.71, 169.12, 158.02, 157.76, 153.08, 149.88, 147.79, 137.69, 136.00, 133.73, 131.29, 130.96, 127.38, 124.88, 123.12, 119.43, 112.68, 110.16, 106.01, 64.41, 60.36, 56.14, 45.20, 38.12, 37.01, 35.23, 14.98. HRMS-ESI (m/z): [M+H]+ (Calcd for C26H31N3O7F) 516.2146;
Found 516.2138. [M+Na]+ (Calcd for C26H30N3O7FNa) 538.1965; Found 538.1963. FTIR (KBr, cm-1) 806.25, 908.47, 1006.84, 1045.42, 1089.78, 1120.64, 1143.79, 1182.36, 1197.79, 1217.08, 1232.51, 1249.87, 1290.38, 1311.59, 1342.46, 1352.10, 1377.17, 1396.46, 1419.61, 1431.18, 1458.18, 1469.76, 1487.12, 1506.41, 1537.27, 1593.20, 1662.64, 1683.86, 1699.29, 1716.65, 2933.73, 3089.96.

Embodiment 9: Preparation of (Z)-2-methoxy-5-(3,4,5-trimethoxystyryl)-phenyl-2-(5-fluoro-2,4-dioxo-3,4-dihydropyrimidin-1(2H)-yl)acetate (Ii)

3,4,4',5-tetramethoxy-3'-hydroxystilbene (CA4, 0.5 g, 1.57 mmol), 2-(5-fluorouracil) acetic acid (IIIa, 1.0 g, 5.31 mmol), anhydrous methylene chloride (30 mL) and DCC (0.5 g) were added into a flask filled with nitrogen. The mixture was stirred for 24 hours at room temperature. The reactant was filtrated while the reaction detected by TLC was complete. The filtration was concentrated and the residue was dissolved in EA. The solution was wished by saturated brine 3 times, dried by anhydrous sodium sulfate and concentrated at vacuum. The crude was subjected to column chromatography to afford product Ii (0.26 g, 34%). 1H-NMR (500 MHz, CDCl3) δ 8.85 (s, 1H), 7.33 (d, J=5 Hz, 1H), 7.18 (d, J=5 Hz, 1H), 6.99 (d, J=5 Hz, 1H), 6.89 (d, J=5 Hz, 1H), 6.51 (m, 4H), 4.67 (s, 2H), 3.88 (s, 3H), 3.84 (s, 3H), 3.72 (s, 6H). 13C-NMR (100 MHz, CDCl3) δ: 165.55, 157.51, 157.25, 152.97, 149.72, 149.69, 141.65, 139.28, 138.68, 137.00, 132.44, 130.15, 129.81, 128.99, 128.66, 128.29, 122.74, 112.14, 105.77, 60.83, 55.98, 55.83, 48.53; HRMS-ESI (m/z): [M+H]+ (Calcd for C24H24N2O8F) 487.1517; Found 487.1557. [M+Na]+ (Calcd for C24H23N2O8FNa) 509.1336; Found 509.1332; FTIR (KBr, cm-1) 1217.08, 1236.37, 1336.67, 1373.32, 1382.96, 1456.26, 1523.76, 1589.34, 1647.21, 1666.50, 1680.00, 1693.50, 1728.22, 2929.87, 3334.92.

Embodiment 10: Preparation of 2-methoxy-5-(3,4,5-trimethoxyphenethyl)-phenyl-2-(5-fluoro-2,4-dioxo-3,4-dihydropyrimidin-1(2H)-yl)acetate (Ij)

According to Embodiment 9, 3,4,4',5-tetramethoxy-3'-hydroxy diphenylethane (IIe, 0.5 g, 1.57 mmol) was reacted with 2-(5-fluorouracil) acetic acid (IIIa, 1.0 g, 5.31 mmol). The crude was subjected to column chromatography to afford product Ij (0.35 g). 1H-NMR (500 MHz, CDCl3) δ 8.59 (s, 1H), 7.36 (d, J=5 Hz 1H), 7.03 (d, J=5 Hz 1H), 6.90 (d, J=5 Hz, 1H), 6.85 (s, 1H), 6.34 (s, 2H), 4.74 (s, 2H), 3.84 (m, 12H), 2.86 (s, 4H). 13C-NMR (100 MHz, DMSO-d6) δ 166.75, 157.99, 157.73, 153.06, 150.02, 149.10, 141.06, 138.89, 138.77, 137.51, 136.02, 134.66, 130.77, 130.43, 127.48, 122.82, 113.34, 106.07, 60.37, 56.35, 56.16, 48.91, 37.96, 36.49. HRMS-ESI (m/z): [M+H]+ (Calcd for C24H26N2O8F) 489.1673; Found 489.1690. [M+Na]+ (Calcd for C24H25N2O8FNa) 511.1493; Found 511.1489; FTIR (KBr, cm-1) 815.89, 975.98, 1004.91, 1024.20, 1124.50, 1151.50, 1170.79, 1242.16, 1269.16, 1330.88, 1381.03, 1421.54, 1463.97, 1510.26, 1589.34, 1668.43, 1701.22, 1774.51, 2841.15, 2933.73, 3003.17, 3070.68.

Embodiment 11: Preparation of (Z)-5-(3,4,5-trimethoxystyryl)-2-methoxyphenyl-3-(5-fluoro-2,4-dioxo-3,4-dihydropyrimidin-1(2H)-yl)propanoate (Ik)

According to Embodiment 9, 3,4,4',5-tetramethoxy-3'-hydroxy stilbene (CA4, 0.5 g, 1.57 mmol) was reacted with 3-(5-fluorouracil) propanoic acid (IIIb, 1.0 g, 5.31 mmol). The crude was subjected to column chromatography to afford product Ik (0.38 g). 1H-NMR (500 MHz, CDCl3) δ 8.93 (s, 1H), 7.58 (d, J=5 Hz, 1H), 7.17 (d, J=5 Hz, 1H), 6.98 (s, 1H), 6.90 (d, J=10 Hz, 1H), 6.50 (s, 2H), 6.50 (d, J=5 Hz, 2H), 4.07 (t, J=10 Hz, 2H), 3.86 (s, 3H), 3.80 (s, 3H), 3.73 (s, 6H), 3.03 (t, J=5 Hz, 2H). 13C-NMR (100 MHz, DMSO-d6) δ 169.28, 158.03, 157.77, 153.04, 150.25, 149.93, 140.85, 139.12, 138.58, 137.22, 132.32, 131.17, 130.84, 130.03, 129.95, 128.62, 127.90, 123.10, 113.13, 106.35, 60.49, 56.28, 55.98, 44.42, 32.51. HRMS-ESI (m/z): [M+H]+ (Calcd for C25H26N2O8F) 501.1673; Found 501.1687. [M+Na]+ (Calcd for C25H25N2O8FNa) 523.1493; Found 523.1501. FTIR (KBr, cm-1) 844.82, 896.90, 1022.27, 1130.29, 1136.07, 1159.22, 1209.37, 1217.08, 1242.16, 1274.95, 1307.74, 1328.95, 1377.17, 1419.61, 1442.75, 1463.97, 1510.26, 1577.77, 1680.00, 1691.57, 1708.93, 1728.22, 1749.44, 2972.31, 3051.39.

Embodiment 12: Preparation of 5-(3,4,5-trimethoxyphenethyl)-2-methoxyphenyl-3-(5-fluoro-2,4-dioxo-3,4-dihydropyrimidin-1(2H)-yl)propanoate (Il)

According to Embodiment 9, 3,4,4',5-tetramethoxy-3'-hydroxy diphenylethane (IIe, 0.5 g, 1.57 mmol) was reacted with 3-(5-fluorouracil) propanoic acid (IIIb, 1.0 g, 5.31 mmol). The crude was subjected to column chromatography to afford product Il (0.41 g). 1H-NMR (500 MHz, CDCl3) δ 8.43 (s, 1H), 7.61 (d, J=10 Hz, 1H), 7.04 (d, J=5 Hz, 1H), 6.91 (d, J=5 Hz, 1H), 6.85 (s, 1H), 6.36 (s, 2H), 4.10 (t, J=10 Hz, 2H), 3.85 (s, 3H), 3.84 (s, 6H), 3.80 (s, 3H), 3.08 (t, J=10 Hz, 2H), 2.86 (s, 4H). 13C-NMR (100 MHz, DMSO-d6) δ169.38, 158.05, 157.79, 153.07, 149.95, 149.21, 140.87, 139.16, 138.60, 137.55, 136.02, 134.58, 131.24, 130.90, 127.14, 122.98, 113.00, 106.05, 60.37, 56.15, 44.54, 37.89, 36.49, 32.60. HRMS-ESI (m/z): [M+H]+ (Calcd for C25H28N2O8F) 503.1830; Found 503.1848. [M+Na]+ (Calcd for C25H27N2O8FNa) 525.1649; Found 525.1645. FTIR (KBr, cm-1) 804.32, 1006.84, 1026.13, 1112.93, 1122.57, 1130.29, 1147.65, 1217.08, 1234.44, 1249.87, 1269.16, 1313.52, 1325.10, 1363.67, 1427.32, 1440.83, 1452.40, 1467.83, 1512.19, 1519.91, 1593.20, 1651.07, 1691.57, 1726.29, 1757.15, 2939.52, 2962.66, 2999.31, 3064.89.

Embodiment 13: Preparation of (Z)-2-methoxy-5-(3,4,5-trimethoxystyryl)-phenyl-4-(5-fluoro-2,4-dioxo-3,4-dihydropyrimidin-1(2H)-yl)butanoate (Im)

According to Embodiment 18, 3,4,4',5-tetramethoxy-3'-hydroxy stilbene (CA4, 0.5 g, 1.57 mmol) was reacted with 4-(5-fluorouracil) butyric acid (IIIc, 1.0 g, 5.31 mmol). The crude was subjected to column chromatography to afford product Im (0.37 g). 1H-NMR (500 MHz, CDCl3) δ 8.79 (s, 1H), 7.42 (d, J=5 Hz, 1H), 7.16 (d, J=5 Hz, 1H), 6.98 (s, 1H), 6.90 (d, J=5 Hz, 1H), 6.52 (s, 2H), 6.50 (d, J=5 Hz, 2H), 3.85 (s, 3H), 3.84 (s, 3H), 3.74 (s, 6H), 2.63 (t, J=10 Hz, 2H), 2.11 (t, J=5 Hz, 2H), 1.27 (m, 2H). 13C-NMR (100 MHz, DMSO-d6) δ170.90, 158.02, 157.77, 153.04, 150.43, 150.09, 139.34, 137.18, 132.38, 129.95, 129.87, 128.68, 127.79, 123.15, 113.09, 106.32, 60.47, 56.30, 55.98, 47.39, 30.54, 24.06. HRMS-ESI (m/z): [M+H]+ (Calcd for C26H28N2O8F) 515.1830; Found 515.1835. [M+Na]+ (Calcd for C26H27N2O8FNa) 537.1649; Found 537.1647; FTIR (KBr, cm-1) 846.75, 883.40, 1024.20, 1134.14, 1155.36, 1174.65, 1205.51, 1240.23, 1276.88, 1317.38, 1328.95, 1357.89, 1381.03, 1421.54, 1452.40, 1512.19, 1581.63, 1616.35, 1627.92, 1662.64, 1689.64, 1720.50, 1741.72, 2933.73.

Embodiment 14: Preparation of 5-(3,4,5-trimethoxyphenethyl)-2-ethoxyphenyl 2-(5-fluoro-2,4-dioxo-3,4-dihydropyrimidin-1(2H)-yl)acetate (In)

According to Embodiment 9, 3,4,5-tetramethoxy-3'-hydroxy 4'-ethoxydiphenylethane (IIf, 0.5 g, 1.57 mmol) was reacted with 2-(5-fluorouracil)acetate acid (IIIa, 1.0 g, 5.31 mmol). The crude was subjected to column chromatography to afford product In (0.38 g). 1H-NMR (300 MHz, DMSO-d6) δ11.99 (s, 1H), 8.13 (s, 1H), 7.05 (d, J=6 Hz, 1H), 7.01 (s, 1H), 6.98 (d, J=6 Hz, 1H), 6.47 (s, 2H), 4.73 (s, 2H), 3.96 (q, J=6 Hz, 2H), 3.69 (s, 6H), 3.57 (s, 3H), 2.75 (d, J=6 Hz, 4H), 1.24 (t, J=6 Hz, 3H); 13C-NMR (100 MHz, DMSO-d6) δ166.68, 157.98, 157.73, 153.06, 149.98, 148.33, 139.28, 137.52, 136.02, 134.67, 130.74, 130.40, 128.42, 127.49, 127.43, 124.80, 122.72, 119.49, 114.47, 110.11, 106.08, 64.63, 60.38, 56.16, 48.85, 37.93, 36.51, 14.99; HRMS-ESI (m/z): [M+H]+ (Calcd for C25H28N2O8F) 503.1830; Found. 503.1848. [M+Na]+ (Calcd for C25H27N2O8FNa) 525.1649; Found 525.1644; FTIR (KBr, cm-1) 808.17, 902.69, 960.55, 975.98, 1002.98, 1041.56, 1116.78, 1168.86, 1242.16, 1265.30, 1330.88, 1346.31, 1381.03, 1419.61, 1456.26, 1510.26, 1589.34, 1666.50, 1699.29, 1714.72, 1778.37, 2939.52, 2981.95, 3066.820.

Embodiment 15: 5-(3,4,5-trimethoxyphenethyl)-2-ethoxyphenyl-3-(5-fluoro-2,4-dioxo-3,4-dihydropyrimidin-1(2H)-yl)propanoate (Io)

According to Embodiment 9, 3,4,5-tetramethoxy-3'-hydroxy 4'-ethoxydiphenylethane (IIf, 0.5 g, 1.57 mmol) was reacted with 3-(5-fluorouracil) propanoic acid (IIIb, 1.0 g, 5.31 mmol). The crude was subjected to column chromatography to afford product Io (0.35 g). 1H-NMR (300 MHz, DMSO-d6) δ11.81 (s, 1H), 8.07 (s, 1H), 6.98 (m, 3H), 6.46 (s, 2H), 3.92 (t, J=6 Hz, 2H), 3.68 (s, 6H), 3.57 (s, 3H), 2.95 (t, J=6 Hz, 2H), 2.74 (s, 4H), 1.24 (t, J=6 Hz, 3H); 13C-NMR (100 MHz, DMSO-d6) δ 169.38, 158.03, 157.77, 153.06, 149.94, 148.40, 140.85, 139.58, 138.58, 137.57, 136.01, 134.59, 131.28, 130.94, 127.08, 122.91, 114.16, 106.05, 64.38, 60.38, 56.15, 44.54, 37.88, 36.51, 32.51, 14.91; HRMS-ESI (m/z): [M+H]+ (Calcd for C26H30N2O8F) 517.1986; Found. 517.2008. [M+Na]+ (Calcd for C26H29N2O8FNa) 539.1806; Found 539.1807; FT-IR (KBr, cm-1) 806.25, 1004.91, 1043.49, 1101.35, 1126.43, 1159.22, 1182.36, 1211.30, 1228.66, 1253.73, 1325.10, 1350.17, 1359.82, 1386.82, 1415.75, 1435.04, 1469.76, 1492.90, 1543.05, 1595.13, 1660.71, 1693.50, 1728.22, 2939.52, 3034.03.

Effects of Embodiments

In order to illustrate the anticancer and antitumor activities of the 5-fluorouracil derivatives provided by the invention, bioactivity experiments are employed to illustrate as shown in the followings:

Compound Activity Test 1

Evaluation of In Vitro Antitumor Activity of Hela Cervical Cancer Tumor Cell Lines with Compounds (MTT Method)

1.1. Test Methods

The cells were cultured in RPMI1640 medium containing 200 mL/L fetal bovine serum so that the cells were kept at logarithmic growth. The cells were inoculated to 96-well plate, with a density of $4$~$8\times10^4$/ml, 37° C., and pre-cultured for 24 hours with added drugs. The drugs were set at 6 concentrations, each has 3 holes. After 48 hours of consequent effect, the nutrient solution was then removed and the cells were left for air-drying. Each hole was then added with cold 500 g/L trichloroacetic acid (TCA) 50 μL (final concentration of 100 g/L). After setting for 60 minutes, it was then rinsed for 4-5 times with ionized water and dried. Each hole then was added with 4 g/L SRB 100 μL left for 30 mins. Then it was rinsed with 10 mL/L acetic acid for 4 times, dried. Then 10 mmol Tris-base 200 μL per hole was added, then shaked and mixed, subsequently, oscillating on the plate oscillator for 5 min. The enzyme-linked immunoassay was used to determine the A value. To calibrate, a blank control was used, with a wavelength of 490 nm. Tumor inhibition rate (%)=(Average A value of the control cell hole−Average A value of the drugged hole A)/Average A value of the control cell hole×100%. The positive control cell holes were CA4, CB1, and CB1N. To calculate the IC50 value, the Logit method was used according to the cell growth inhibition rate of different concentrations of the drug.

1.2. Test Results

TABLE 1

In vitro proliferation inhibition activity of embodiment compound (Ia-Io) against Hela cervical cancer cell line (IC50/nmol/L)

| Compound number | Substituent group | | | | $IC_{50}$ (nmol/L) |
|---|---|---|---|---|---|
| | $L_1$ | $L_2$ | R | X | |
| Ia | —CH=CH— | —CH$_2$— | OMe | NH | 45.99 |
| Ib | —CH$_2$CH$_2$— | —CH$_2$— | OMe | NH | 29.12 |
| Ic | —CH=CH— | —CH$_2$CH$_2$— | OMe | NH | 28.99 |
| Id | —CH$_2$CH$_2$— | —CH$_2$CH$_2$— | OMe | NH | 29.83 |
| Ie | —CH=CH— | —CH$_2$CH$_2$CH$_2$— | OMe | NH | 68.82 |
| If | —CH$_2$CH$_2$— | —CH$_2$CH$_2$CH$_2$— | OMe | NH | 28.80 |
| Ig | —CH=CH— | —CH$_2$— | OEt | NH | 47.12 |
| Ih | —CH$_2$CH$_2$— | —CH$_2$CH$_2$— | OEt | NH | >370 |
| Ii | —CH=CH— | —CH$_2$— | OMe | O | 31.41 |
| Ij | —CH$_2$CH$_2$— | —CH$_2$— | OMe | O | 32.33 |
| Ik | —CH=CH— | —CH$_2$CH$_2$— | OMe | O | 29.57 |
| Il | —CH$_2$CH$_2$— | —CH$_2$CH$_2$— | OMe | O | 29.61 |
| Im | —CH=CH— | —CH$_2$CH$_2$CH$_2$— | OMe | O | 30.03 |
| In | —CH$_2$CH$_2$— | —CH$_2$— | OEt | O | 39.98 |
| Io | —CH$_2$CH$_2$— | —CH$_2$CH$_2$— | OEt | O | 34.25 |
| CA4 | / | / | / | / | 400 |
| 5-FU | / | / | / | / | 113.24 |

All data contained three parallel samples with ± S.D. in each group.

1.3 Experimental Results Analysis

Using CA4 and 5-fluorouracil as positive control drugs, the in vitro proliferation inhibition activity of 5-fluorouracil derivative (Ia-Jo) with the invention was evaluated for Hela cervical cancer cell line (MTT method). The IC50 values of 5-fluorouracil and CA4 were 113.24 nM and 400 nM under the same test conditions respectively, while the IC50 values of all splices were below 70 nM, in which the best active compound Ic inhibited the proliferation activity of Hela cervical cancer cell line in vitro was 4 times compared to 5-fluorouracil and 14 times compared to CA4.

Compound Activity Test II

Evaluation of In Vitro Antitumor Activity of Compounds on Multiple Tumor Cell Lines (CCK-8 Method)

2.1. Experimental Methods

Take the living cells with more than 90% cells for testing. The cell proliferation inhibition test was performed using the EnoGeneCell™ Counting Kit-8 (CK-8) cell viability test kit. The cell was digested, counted and prepared into a cell suspension with a concentration of 1×10$^5$/mL. 100 μL cell suspension (1×10$^4$ cells per hole) was added to each hole in the 96-well plate. The 96-well plate was cultured in a 37° C., 5% CO$_2$ incubator for 24 hours. With every hole added with 100 μL respective drugged cultured medium, control groups were set up, including negative control group, solvent control group, and positive control group. Each group has 5 holes. The 96-well plates were cultured at 37° C., in 5% CO$_2$ incubator for 72 hours. Afterward, 10 μL CCK-8 solution was added to each hole, and the culture plate was incubated in the incubator for 4 hours, and the OD value at 450 nm was determined by enzyme labeling instrument. The inhibition rate and IC50 value of these compounds on tumor cells such as human gastric cancer cell MGC-803, human liver cancer cell HepG2, human lung cancer cell A549 and human breast cancer cell MDA-MB-231 were calculated.

2.2 Experimental Results

TABLE 2

The inhibition rate and IC50 value of compounds on the proliferation activity of multiple tumor cell lines in vitro.

| | $IC_{50}$(umol/L) | | | |
|---|---|---|---|---|
| Compounds | MGC-803 | HepG2 | A549 | MDA-MB-231 |
| 5-FU | 62.5 | 0.004 | 34.89 | 97.04 |
| CA4 | 0.02058 | 1285 | 0.00254 | 0.0033 |
| Ia | 64.15 | 0.01245 | 27.53 | 111.8 |
| Ib | 1.86 | <0.19 | <0.19 | 3.21 |
| Ic | 48.5 | 150.5 | 57.93 | 122.2 |
| Id | 50.64 | 110.5 | 38.02 | 70.19 |
| Ig | 25.82 | 39.4 | 59.86 | 60.22 |
| Ih | 23.18 | 170.7 | 15.23 | 60.56 |
| Ii | <0.0003 | 0.02278 | <0.0003 | 0.3997 |
| Ij | <0.0003 | 0.1414 | <0.0003 | 15.41 |
| Ik | <0.0003 | 7.333 | <0.0003 | 80.65 |
| Il | <0.0003 | 0.0004 | <0.0003 | 0.00025 |
| In | 19.29 | 468.3 | 4.257 | 101.7 |
| Io | 0.6092 | 0.0017 | 0.0003 | 2.57 |

2.3 Experimental Results Analysis

All the tested 5-fluorouracil derivatives showed inhibitory activity against human gastric cancer cells MGC-803, human hcc cells HepG2, human lung cancer cells A549, and human breast cancer cell MDA-MB-231. Compared with the positive drugs CA4 and 5-fluorouracil, the spliced 5-fluorouracil derivatives showed significantly improved activity, indicating that the spliced product of 5-fluorouracil derivatives had synergistic effect in vivo. Upon further observation, the number of alkyl carbons (n=1, 2, 3, 4) on the linked base L2 has some effect on the activity of the product. Overall, the activity is better when n=2.

Compound Activity Test III

Antitumor rate of oral administration of the compound towards MGC-803 mice with transplanted tumor 3.1 Experimental Methods After 1 week of adaptation, the mice were inoculated with gastric cancer MGC-803 tumor tissue subcutaneously. After the tumor grew for 100-300 mm$^3$, the animals were randomly grouped. For the drug group, each group of each compound had 6 mice, and 12 mice were in the control group. The intragastric administration was employed and the dosage of Ii, Ij, Ik and Il was 25 and 50 mg/kg. The positive control was CA4, the administration time was d0, d2, d4, d6, d8, d10, d12 days, 7 times in total. The tumor size was measured 3 times per week, together with mice weight. The mice were executed 14 days after inoculation and the tumor mass was taken and measured for its weight. The tumor inhibition rate was calculated as tumor weight inhibition rate, and the formula is tumor weight inhibition rate %=(1−treatment group average tumor weight/control group average tumor weight)×100%.

3.2. Experimental Results

According to the administration plan, the above compounds can significantly inhibit the growth of transplanted tumors in MGC-803 mice. About 8 days after administration, ii, ij, ik, il administration group showed that the tumors had a tendency to shrink. The tumor inhibition rate of 50 (mg/kg) dose was over 80%.

TABLE 3

Tumor inhibition rate of MGC-803 mice transplanted with oral administration drugs (%)

| Group | Ii | | Ij | | Ik | | Il | |
|---|---|---|---|---|---|---|---|---|
| Dosage (mg/kg) | 25 | 50 | 25 | 50 | 25 | 50 | 25 | 50 |
| Tumor inhibition rate (%) | 62 | 85 | 53 | 80 | 48 | 75 | 65 | 90 |

3.3. Experimental Results Analysis

Four compounds with strong in vitro activity (ii, ij, ik, il) were selected for the test of the tumor inhibition rate of MGC-803 mice transplanted tumor. When the tumor inhibition rate was over 80% at oral administration of 50 mg/kg, and the effective oral dose was about one tenth of the 5-fluorouracil 1D50 value (230 mg/kg), provided that it is safe. Tests and calculations have proved that a wider range of 5-500 mg/kg is also effective. The specific situation should be selected according to the type of cancer or tumor and the severity of the condition, as 25 mg/kg and 50 mg/kg are just the relatively better choice.

Toxicity Test of Compounds

Acute Toxicity Test of Single Gastric Administration in Mice 4.1. Experimental Methods Kunming mice (weight 17-22 g, equal male and female) were randomly grouped according to body weight, with 10 mice maximum per dose group in the experiment. And with a maximum dose of 1500 mg/kg, and a ratio of 0.9, the mice were divided into 10 dose groups. The dosages of the tested drugs were 1500, 1350, 1215, 1093, 984, 885, 797, 717, 645, and 581 mg/kg. Given by single intraperitoneal injection and a single intragastric injection, observations were done after 0.25 h, 0.5 h, 1 h, 2 h, 4 h, and 24 h respectively. The mortality rate was recorded. Afterward, the groups were observed once everyday, and the mortality rate was recorded for 14 days. On day 15, the living mice were sacrificed for pathological dissection.

4.2. Experimental Results

After a single dose of intragastric administration and a high dose of 40 min-1 hr, there were casualties, and no obvious residual solution was found in dissection, indicating that the drug was absorbed quickly. The remaining mice died mainly on the first 2 days after a single intraperitoneal injection, and no mice died after the 5th day. Dissections upon dead mice showed that there was no anomaly on the viscera including heard, lungs, liver, spleen, kidneys, etc. The alive mice showed diarrhea, yet not severe, indicating that the tested drugs mainly cause acute toxic effect with no obvious delayed toxicity.

TABLE 4

Results of acute toxicity test for a single intragastric administration in mice

| Compound | Ii | Ij | Ik | Il | 5-FU | CA4 | Erianin |
|---|---|---|---|---|---|---|---|
| LD$_{50}$ (mg/kg) | 1059 | 1015 | 1185 | 1228 | 230 | 1276 | 2531 |
| 95% Confidence Limit | 815-1395 | 789-1298 | 840-1138 | 1050-1438 | 210-250 | 1047-1255 | 2511-2553 |

4.3 Experimental Results Analysis

From the experimental results shown in table 4, it can be seen that the tested compounds ii, ij, ik, il had acute LD50 above 1000 mg/kg, and the toxicity is very low. This means the 5-fluorouracil derivatives of the invention (distyrene and diphenylethane fragments spliced with 5-fu twins) had low toxicity (lower than 5-FU, and similar to CA4), which means it is quite safe.

Summary of Experiments on Bioactivity Testing

5-Fluorouracil is an anti-metabolic anti-tumor drug with a broad anti-tumor spectrum. Side effects such as bone marrow suppression and severe gastrointestinal reactions etc. has reduced patients' tolerance to the treatment. This type of compound has high water solubility and low liposolubility. Styrene/alkane compounds, as a class of tubulin inhibitors, have tumor vascular targeting effect, with high liposolubility and poor water solubility.

This invention creatively splices two kinds of antitumor drugs with different mechanisms of action in the form of chemical bonds, and designs a novel synthetic route to synthesize the compounds of these specific novel structures (new structure). Through the above biological activity tests on the in vitro activity of the typical cancer cell line and the tumor inhibition activity in mice, the advantages of the proposed 5-fluorouracil derivatives with two kinds of antitumor drugs were shown, which served its purpose of creating a synergistic effect. Therefore, this compound can improve the pharmaceutical properties of two kinds of antitumor drugs, and improve the anti-tumor activity and oral bioavailability of the styrene/alkane compounds. Furthermore, through vascular targeting effect of styrene/alkane fragments, 5-fluorouracil can be directed to tumor cells, thereby reducing the toxic side effects of 5-fluorouracil.

As a common knowledge of experts in this field, the molecular structure of the 5-fluorouracil derivative of this invention contains a distyrene and diphenylethane class fragment, which has the same effect as the tubulin aggregation inhibitor CA4. So the 5-fluorouracil derivative of this invention can be used as a tubulin aggregation inhibitor, or as a preparation agent for tubulin aggregation inhibitor production.

As described in the background, the 5-fluorouracil derivatives of The invention can interfere with tubulin aggregation and thus inhibit the formation of tumor blood vessels, so they can also be used as anti-tumor vascular disruptors or as a preparation agent for the production of anti-tumor vascular disruptors.

Furthermore, because of its inhibitory effect on angiogenesis, it must also be able to treat diseases caused by abnormal neovascularization, or to prepare drugs for the treatment of diseases caused by abnormal neovascularization. Current known diseases of such kind include rheumatoid arthritis, diabetic retinopathy, precocious retinopathy, retinal venous occlusion, psoriasis, erythematous acne, Kaposi sarcoma, specific reactive keratitis, keratoconjunctivitis, neovascular glaucoma, bacterial ulcer, fungal ulcer, simple scar rash infection, zoster infection, protozoa infection, *mycobacterium* infection, polyarteritis, sarcoid tumor, scleritis, flushing, xerostomia and xerophthalmia syndrome, systemic lupus erythematosus, AIDS syndrome, syphilis.

The 5-fluorouracil derivative provided by the invention has inhibitory activity on human gastric cancer cells MGC-803, human liver cancer cells HepG2, human lung cancer cells A549 and human breast cancer cells MDA-MB-231, and it is not difficult to predict its therapeutic effect on other clinical cancers, tumors, including lung cancer, non-small cell carcinoma, liver cancer, pancreas cancer, stomach cancer, bone cancer, esophagus cancer, breast cancer, prostate cancer, testicular cancer, colon cancer, ovarian cancer, bladder cancer, cervical cancer, melanoma, squamous cell carcinoma, basal cell carcinoma, adenocarcinoma, sebaceous gland carcinoma, sebaceous gland carcinoma, papillary carcinoma Cystic carcinoma, papillary carcinoma, cystic carcinoma, cystic carcinoma, myeloid carcinoma, bronchial carcinoma, osteocyte carcinoma, epithelial carcinoma, cholangiocarcinoma, choriocarcinoma, embryo cancer, spermatogonial carcinoma, Wilms carcinoma, glial carcinoma, astrocytoma, neuroblastoma, craniopharyngioma, ependymoma, pinealoma, hematoblastoma, vocal cord neuroma, meningioma, neuroblastoma, optic neuroma, retinocytoma, neurofibromatosis, fibrosarcoma, fibroblastoma, fibroadenoma, fibrochondroma, fibrocystic tumor, fibromylinoma, fibroosteoma, fibromyxa, fibromyxa, fibromatosis, fibro papilloma, fibroid, papilloma, sarcoma, mucous sac, myxochondroma, myxosarcoma, myxosarcoma, myxochondrosarcoma, mucinous adenoma, myxoma, myxocytoma, myxocytoma, myxocytoma, lipoma, lipoma, lipoma, lipoma, lipoma, lipoma, lipoma, lipoma, lipoma, lipoma, lipoma, lipoma, lipoma, lipoma, lipoma, lipoma, lipoma Litoma, chondrosarcoma, chondroma, chondromyoma, chordoma, chorionic adenoma, villoepithelioma, chorionic cell tumor, osteosarcoma, osteoblastoma, osteochondroma, osteochondroma, osteocystoma, osteo dentinoma, bone fibroma, osteofibroma, hemangioma, hemangioma, hemangioma, hemangioma, hemangioma, hemangioma, hemangioma, hemangichondroma, hemangioblastoma, hemangioblastoma, hemangioblastoma, hemangioma, hemangioma, hemangioma, hemangioma, hemangioma, hemangioma, hemangioblastoma, hemangioblastoma, hemangioma, hemangioblastoma, hemangioblastoma, hemangioperioma, hemangioblastoma, hemangioblastoma, lymphosarcoma, lymphadenoma, lymphangioma, lymphoma, lymphoma, lymphoma, lymphangioma, lymphangioma, lymphangioma, hemangioblastoma, hemangioblastoma, hemangioblastoma, hemangioblastoma, endothelioma, synovialoma, synovial sarcoma, mesoma, leiomyoma, leiomyoma, leiomyoma, leiomyoblastoma, leiomyoblastoma, leiomyoblastoma leiomyoma, leiomyoma, rhabdomyosarcoma, rhabdomyosarcoma, rhabdomyosarcoma, acute lymphoblastic leukemia, acute myeloid leukemia, chronic cell/erythrocytosis, lymphoma, or multiple myeloma.

Furthermore, kunming mice were used in the experiment to demonstrate that the compound had a significant in vivo inhibitory effect on the transplanted tumor in MGC-803 mice. And it would also be able to demonstrate therapeutic effect on cancer and tumor in other non-human mammals.

In addition, other than the above anti-tumor and anti-cancer effects, this invention can also be administered alone or in combination with other anti-cancer and anti-tumor drugs as a composition (compound) to treat tumor or cancer. See Cancer Principles and Practice of Oncology specifically (edited by V. T. Devita and S. Hellman, 6th ed. (2001), Lipincott Williams & Wilkins Publishers).

General technicians in the field should be able to identify which combination of drugs can be used based on the specific characteristics of the drug and the cancer involved. These anticancer agents include, but are not limited to: HDAC inhibitors, estrogen receptor regulators, androgen receptor regulators, retinoid receptor regulators, cytotoxicity/cell growth inhibitors, anti-proliferative agents, isoprene-based protein transferase inhibitors, HMG-CoA reductase inhibitors, HIV protease inhibitors, reverse transcriptase inhibitors and other angiogenic inhibitors, inhibitors of cell proliferation and survival signaling, apoptosis inducers and agents that interfere with cell cycle checkpoints.

In conclusion, this new invention of new structural compound obtained by splicing the two types of antitumor drugs has the advantages of the two types of antitumor drugs, as well as the synergistic effect, with a bright application and development prospect.

The above embodiment is a preferred case of the invention and is not used to limit the protection range of the invention.

What is claimed:

1. A compound of formula VI:

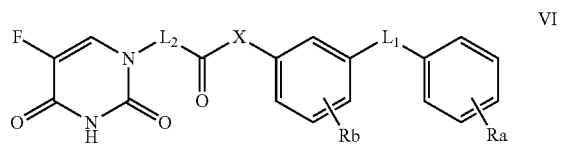

wherein:
1) Ra is a mono-substituted, di-substituted, tri-substituted, tetra-substituted or penta-substituted phenyl group, in which one or more hydrogens are substituted by (C1-C4) alkoxy or fluorine-substituted (C1-C4) alkoxy;
2) Rb is a mono-substituted, di-substituted, tri-substituted, or tetra-substituted phenyl group, in which one or more hydrogens are substituted by (C1-C4) alkoxy or fluorine-substituted (C1-C4) alkoxy;
3) the linking group L1 is —CH═CH— or —CH$_2$CH$_2$—;
4) the linking group L2 is —CH$_2$—, —CH$_2$CH$_2$—, or —CH$_2$CH$_2$CH$_2$—;
5) the group X is independently selected from the group of a bond, O, and —NH—.

2. The compound according to claim 1, wherein:
1) Ra is a tri-substituted phenyl group, in which three hydrogens are substituted by —OMe, —OCF$_3$, —OCF$_2$H or —OCFH$_2$,
2) Rb is a mono-substituted phenyl group, in which one hydrogen is substituted by —OMe, or —OEt.

3. The compound according to claim 1, characterized in that its structure characteristic is shown as formula I:

(I)

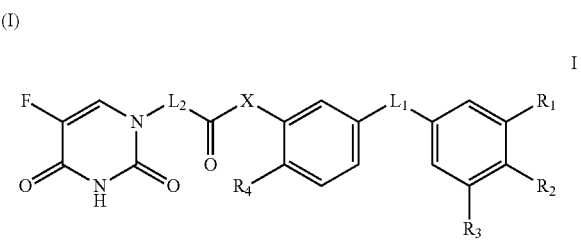

wherein:
1) each R1, R2 or R3 is independently (C1-C4) alkoxy, or fluorine-substituted (C1-C4) alkoxy;
2) R4 is (C1-C4) alkoxy or fluorine-substituted (C1-C4) alkoxy.

4. The compound according to claim 3, wherein:
each R1, R2, R3 or R4 is independently —OCH$_3$, —OC$_2$H$_5$, —OCF$_3$, —OCF$_2$H or —OCFH$_2$.

5. The compound according to claim 1, wherein said compound is selected from the group consisting of:
Compound Ia: (Z)-2-(5-fluoro-2,4-dioxo-3,4-dihydropyrimidin-1(2H)-yl)-N-(2-methoxy-5-(3,4,5-trimethoxystyryl (phenyl) acetamide,
Compound Ib: 3-(5-fluoro-2,4-dioxo-3,4-dihydropyrimidin-1(2H)-yl)-N-(2-methoxy-5-(3,4,5-trimethoxyphenethyl(phenyl) acetamide, Compound Ic: (Z)-3-(5-fluoro-2,4-dioxo-3,4-dihydropyrimidin-1(2H)-yl)-N-(2-methoxy-5-(3,4,5-trimethoxystyryl(phenyl) propanamide, Compound Id: 3-(5-fluoro-2,4-dioxo-3,4-dihydropyrimidin-1(2H)-yl)-N-(2-methoxy-5-(3,4,5-trimethoxyphenethyl(phenyl) propanamide, Compound Ie: (Z)4[3]]4-(5-fluoro-2,4-dioxo-3,4-dihydropyrimidin-1(2H)-yl)-N-(2-methoxy-5-(3,4,5-trimethoxystyryl(phenyl)butyrylamide, Compound If: 4-(5-fluoro-2,4-dioxo-3,4-dihydropyrimidin-1(2H)-yl)-N-(2-methoxy-5-(3,4, 5-trimethoxyphenethyl(phenyl)butyrylamide, Compound Ig: N-(2-ethoxy-5-(3,4,5-trimethoxyphenethyl(phenyl)-2-(5-fluoro-2,4-dioxo-3,4-dihydropyrimidin-1(2H)-yl) acetamide, Compound Ih: N-(2-ethoxy-5-(3,4,5-trimethoxyphenethyl(phenyl)-3-(5-fluoro-2,4-dioxo-3,4-dihydropyrimidin-1(2H)-yl) propanamide, Compound Ii: (Z)-2-methoxy-5-(3,4,5-trimethoxystyryl)-phenyl-2-(5-fluoro-2,4-dioxo-3,4-dihydropyrimidin-1(2H)-yl)acetate, Compound Ij: 2-methoxy-5-(3,4,5-trimethoxyphenethyl)-phenyl: 2-(5-fluoro-2,4-dioxo-3,4-dihydropyrimidin-1(2H)-yl)acetate, Compound Ik: (Z)-2-methoxy-5-(3,4,5-trimethoxystyryl)-phenyl-3-(5-fluoro-2,4-dioxo-3,4-dihydropyrimidin-1(2H)-yl)propanoate, Compound Il: 2-methoxy-5-(3,4,5-trimethoxyphenethyl)-phenyl-3-(5-fluoro-2,4-dioxo-3,4-dihydropyrimidin-1(2H)-yl)propanoate, Compound Im: (Z)-2-methoxy-5-(3,4,5-trimethoxystyryl)-phenyl-4-(5-fluoro-2,4-dioxo-3,4-dihydropyrimidin-1(2H)-yl)butyrate, Compound In: 2-ethoxy-5-(3,4,5-trimethoxyphenethyl)-phenyl-2-(5-fluoro-2,4-dioxo-3,4-dihydropyrimidin-1(2H)-yl)acetate, and Compound Io: 2-ethoxy-5-(3,4,5-trimethoxyphenethyl)-phenyl-3-(5-fluoro-2,4-dioxo-3,4-dihydropyrimidin-1(2H)-yl)propanoate.

6. A pharmaceutical composition containing the compound of claim 1 and a pharmaceutically acceptable carrier.

7. The pharmaceutical composition according to claim 6, characterized in that it is a dosage form selected from the group consisting of: lyophilized powder, powder, injection, liposome, emulsion, microcapsule, suspension or solution for intravenous administration; granules, tablets, capsules or syrup for oral administration; and suppository.

* * * * *